US008721584B2

(12) United States Patent
Braithwaite et al.

(10) Patent No.: US 8,721,584 B2
(45) Date of Patent: May 13, 2014

(54) METHODS AND SYSTEMS FOR DETERMINING AN INTRAVENOUS INSULIN INFUSION RATE TO CORRECT HYPERGLYCEMIA OF A PATIENT, TO MAINTAIN EUGLYCEMIA OF A PATIENT, AND TO PREVENT HYPOGLYCEMIA OF A PATIENT

(75) Inventors: Susan S. Braithwaite, Skokie, IL (US); Guillermo E. Umpierrez, Atlanta, GA (US)

(73) Assignees: The University of North Carolina at Chapel Hill, Chapel Hill, NC (US); Emory University, Atlanta, GA (US)

( * ) Notice: Subject to any disclaimer, the term of this patent is extended or adjusted under 35 U.S.C. 154(b) by 1046 days.

(21) Appl. No.: 12/513,426

(22) PCT Filed: Nov. 2, 2007

(86) PCT No.: PCT/US2007/023071
§ 371 (c)(1),
(2), (4) Date: Feb. 1, 2010

(87) PCT Pub. No.: WO2008/057384
PCT Pub. Date: May 15, 2008

(65) Prior Publication Data
US 2010/0137788 A1 Jun. 3, 2010

Related U.S. Application Data

(60) Provisional application No. 60/856,250, filed on Nov. 2, 2006.

(51) Int. Cl.
*A61M 31/00* (2006.01)
(52) U.S. Cl.
USPC .......................................... 604/66

(58) Field of Classification Search
USPC ........................................... 604/66
See application file for complete search history.

(56) References Cited

U.S. PATENT DOCUMENTS

2003/0195404 A1* 10/2003 Knobbe et al. ............... 600/365
2003/0224355 A1 12/2003 Bell et al.
(Continued)

OTHER PUBLICATIONS

Notification of Transmittal of the International Search Report and the Written Opinion of the International Searching Authority, or the Declaration for International Application No. PCT/US07/23071 (Jun. 24, 2008).

(Continued)

*Primary Examiner* — Nicholas Lucchesi
*Assistant Examiner* — Diva K. Chander
(74) *Attorney, Agent, or Firm* — Jenkins, Wilson, Taylor & Hunt, P.A.

(57) ABSTRACT

Methods and systems for determining an intravenous infusion rate to correct hyperglycemia of a patient, to maintain euglycemia of a patient, and to prevent hypoglycemia are disclosed. In one aspect, a method for determining an intravenous insulin infusion rate to correct hyperglycemia of a patient includes estimating an insulin infusion maintenance rate to maintain euglycemia in a patient. Further, a relationship between a current blood glucose concentration of the patient and a target blood glucose concentration may be determined. An insulin infusion rate may be determined based on the estimated insulin infusion maintenance rate and based on the relationship between the current blood glucose concentration and the target blood glucose concentration. A glycemic response of the patient may be measured while using the determined insulin infusion rate. The insulin infusion maintenance rate is re-estimated based on the glycemic response of the patient at a previous insulin infusion rate.

7 Claims, 24 Drawing Sheets

(56) References Cited

U.S. PATENT DOCUMENTS

2005/0055010 A1    3/2005   Pettis et al.
2005/0171503 A1*   8/2005   Van Den Berghe et al. .. 604/504

OTHER PUBLICATIONS

Kitabchi et al., "Hyperglycemic Crises in Adult Patients with Diabetes: A Consensus Statement from the American Diabetes Association," Diabetes Care, vol. 29, No. 12, pp. 2739-2748 (Dec. 2006).
Braithwaite et al., "Performance of a Dose-Defining Insulin Infusion Protocol Among Trauma Service Intensive Care Unit Admission," Diabetes Technol. Ther., vol. 8, No. 4, pp. 476-488 (Nov. 4, 2006).
Van den Berghe et al., "Intensive Insulin Therapy in the Medical ICU," N Engl J Med vol. 354, No. 5, pp. 449-461.
Krinsley, "Effect of an intensive glucose management protocol on the mortality of critically ill adult patients," Mayo Clin Proc, vol. 79, No. 8, pp. 992-1000 (Aug. 2004).
Krinsle, Association Between Hyperglycemia and Increased Hospital Mortality in a Heterogeneous Population of Critically Ill Patients, Mayo Clin Proc, vol. 78, pp. 1471-1478 (2003).
Markovitz et al., "Description and evaluation of a glycemic management protocol for diabetic patients undergoing heart surgery," Endocrine Practice, vol. 8, No. 1, pp. 10-18 (Jan./Feb. 2002).
Van den Berghe et al., "Intensive Insulin Therapy in Critically Ill Patients," N Engl J Med, vol. 345, No. 19, pp. 1359-1367 (Nov. 8, 2001).

* cited by examiner

METHODS AND SYSTEMS FOR DETERMINING AN INTRAVENOUS INSULIN INFUSION RATE TO CORRECT HYPERGLYCEMIA OF A PATIENT, TO MAINTAIN EUGLYCEMIA OF A PATIENT, AND TO PREVENT HYPOGLYCEMIA OF A PATIENT

RELATED APPLICATIONS

This application claims the benefit of U.S. Provisional Patent Application Ser. No. 60/856,250, filed Nov. 2, 2006; the disclosure of which is incorporated herein by reference in its entirety.

TECHNICAL FIELD

The subject matter disclosed herein relates to methods and systems for determining an insulin infusion rate for a patient. In particular, the subject matter disclosed herein relates to methods and systems for determining an intravenous insulin infusion rate to correct hyperglycemia of a patient, to maintain euglycemia of a patient, and to prevent hypoglycemia of a patient.

BACKGROUND

Among cardiac patients and critically ill populations, hyperglycemia is associated with increased mortality. Following cardiac surgery specifically, wound infections and other morbidities are increased among patients having diabetes or uncontrolled hyperglycemia. Strict glycemic control during the perioperative time period can reduce morbidities and mortality. Some of the most striking outcome results have been achieved with the user of perioperative intravenous insulin infusions. Outside of the intensive care unit, and after the third postoperative day in the hospital, or during subsequent outpatient follow-up after heart surgery, concerning the importance of glycemic control or the methods used to achieve control, there are less population-specific data than during the earlier timeframe immediately following surgery in relation to outcomes. Nevertheless, it is reasonable to apply hospital and outpatient glycemic standards for glycemic control that have been advocated for hospitalized and general populations.

The default order for a busy medical practitioner at the time of transition from intravenous insulin infusion, if an institutional standardized sliding scale exists, is likely to be a "sliding scale". Sliding scale refers to an algorithm that assigns blood glucose test times and short- or rapid-acting insulin, in preassigned doses that often are arbitrarily determined without consideration for the insulin sensitivity of the patient to be administered at predetermined times according to the severity of the hyperglycemia, without consideration for carbohydrate exposure, and to be used without concomitant orders for intermediate- or long-acting insulin or scheduled mealtime insulin.

Use of sliding scale insulin as monotherapy results in poor control. Hyperglycemia and sometimes ketoacidosis result from omission of scheduled insulin. Sliding scale insulin doses, given reactively after development of hyperglycemia, are implicated in the causation of hospital hypoglycemia, especially in the presence of renal failure. Accordingly, there exists a long-felt need for improved methods and systems for determining an intravenous insulin infusion rate to correct hyperglycemia of a patient, to maintain euglycemia of a patient, and to prevent hypoglycemia of a patient.

SUMMARY

Methods and systems for determining an intravenous infusion rate to correct hyperglycemia of a patient, to maintain euglycemia of a patient, and to prevent hypoglycemia are disclosed. In one aspect, a method for determining an intravenous insulin infusion rate to correct hyperglycemia of a patient includes estimating an insulin infusion maintenance rate to maintain euglycemia in a patient. Further, a relationship between a current blood glucose concentration of the patient and a target blood glucose concentration may be determined. An insulin infusion rate may be determined based on the estimated insulin infusion maintenance rate and based on the relationship between the current blood glucose concentration and the target blood glucose concentration. A glycemic response of the patient may be measured while using the determined insulin infusion rate. The insulin infusion maintenance rate is re-estimated based on the glycemic response of the patient at a previous insulin infusion rate. Further, the steps of associating the current blood glucose concentration, determining the insulin infusion rate, measuring glycemic response, and re-estimating the insulin infusion maintenance rate may be repeatedly performed. The estimating step during each $n^{th}$ iteration may be utilized to determine the insulin infusion rate of each $(n+1)^{th}$ iteration, where n is an integer.

According to one aspect, a method for determining an intravenous insulin infusion rate to maintain euglycemia of a patient includes estimating an insulin infusion maintenance rate to maintain euglycemia in a patient. Further, a relationship between a current blood glucose concentration of the patient and a target blood glucose concentration is determined. The method also includes determining an insulin infusion rate based on the estimated insulin infusion maintenance rate and based on the relationship between the current blood glucose concentration and the target blood glucose concentration. An initial estimated insulin infusion maintenance rate can be a protocol parameter having different values according to patient population. A glycemic response of the patient to an insulin infusion given to the patient using the determined insulin infusion rate is measured. Further, a next insulin infusion maintenance rate is determined by one of (1) re-estimating the insulin infusion maintenance rate based on the glycemic response of the patient at a previous insulin infusion rate, (2) carrying forward a previous insulin infusion maintenance rate unchanged to become the next insulin infusion maintenance rate, or (3) based on criteria for risk of hypoglycemia setting the next insulin infusion maintenance rate to be a percentage less than the previous insulin infusion maintenance rate. The steps, except for initially estimating an insulin infusion maintenance rate, may be repeatedly performed. Further, the next insulin infusion maintenance rate during each $n^{th}$ iteration may be utilized to calculate the insulin infusion rate of each $(n+1)^{th}$ iteration, where n is an integer.

According to one aspect, a method for determining an intravenous insulin infusion rate to prevent hypoglycemia includes determining that a blood glucose concentration of a patient is within a euglycemic range. In response to determining that the blood glucose concentration of the patient is within the euglycemic range but below a target value blood glucose concentration, calculating an insulin infusion rate based on an exponential function associating a blood glucose concentration and an insulin infusion maintenance rate with an assignment of the next insulin infusion rate.

The subject matter described herein may be implemented using a computer program product comprising computer executable instructions embodied in a computer readable medium. Exemplary computer readable media suitable for implementing the subject matter described herein include chip memory devices, disc memory devices, application specific integrated circuits, programmable logic devices, and downloadable electrical signals. In addition, a computer program product that implements a subject matter described herein may reside on a single device or computing platform or maybe distributed across multiple devices or computing platforms. This and other objects as may become apparent from the present disclosure are achieved, at least in whole or in part, by the subject matter described herein.

BRIEF DESCRIPTION OF THE DRAWINGS

Preferred embodiments of the subject matter described herein will now be explained with reference to the accompanying drawings of which.

DETAILED DESCRIPTION

Improved methods and systems for determining an intravenous insulin infusion rate to correct hyperglycemia of a patient, to maintain euglycemia of a patient, and to prevent hypoglycemia of a patient are disclosed herein. In particular, methods and system for intravenous insulin infusion for patients who require exogenous insulin to maintain glycemic control within a target range of blood glucose concentration (BG). For some hospital populations, intravenous insulin therapy reduces mortality and morbidities, but treatment may be complicated by hypoglycemia.

The methods and systems described herein may estimate a maintenance requirement for insulin under ambient conditions of illness, carbohydrate exposure, and concomitant therapies. From knowledge of the maintenance requirement, appropriate corrective adjustments of insulin infusion rate may be assigned during upward or downward trend of blood glucose. Whereas the true maintenance requirement may be defined during euglycemic intervals of stability, the intravenous infusion maintenance rate (MR) may be estimated prior to attainment of euglycemia by observing glycemic response to insulin infusion.

For correction of hyperglycemia, after estimation of a maintenance rate of insulin infusion, a linear function or an asymptotic negative exponential function associating a blood glucose concentration and a maintenance rate of insulin infusion to insulin infusion rate for a future iteration of the algorithm may be used. Further, for maintaining euglycemia, an exponential function associating an insulin infusion rate to blood glucose concentration and to maintenance rate may be used in the euglycemic range so as to reduce the risk of hypoglycemia during patient treatment. Further, the methods and systems disclosed herein can estimate a maintenance rate cross step next estimate ($MR_{csne}$), which provides an estimate of the true maintenance rate, for estimating the maintenance rate in response to a rate of change of blood glucose concentration and a previous insulin infusion rate. Methods and systems disclosed herein may be used to correct hyperglycemia, if present, to maintain target range control, and to restrain the rate of ascent of blood glucose concentration during euglycemia.

Figure 1:
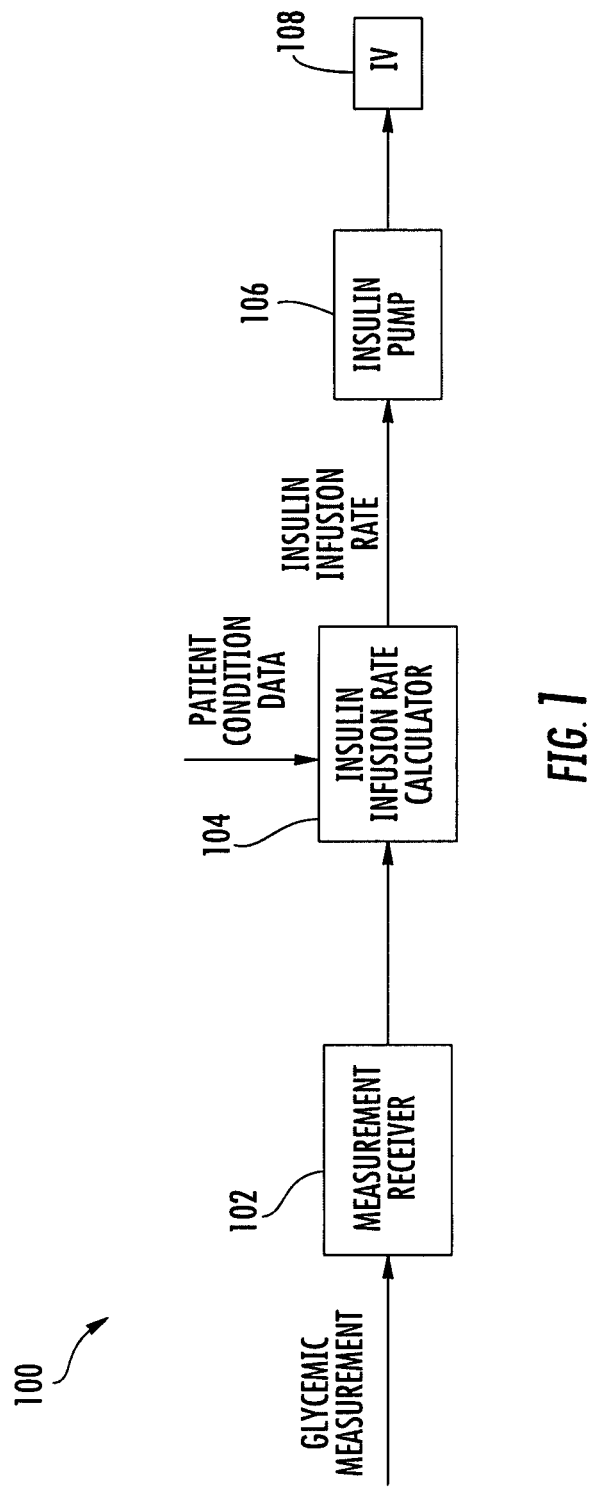
FIG. 1 illustrates a block diagram of an exemplary system for determining an intravenous insulin infusion rate to correct hyperglycemia according to an embodiment of the subject matter disclosed herein.

According to one aspect, the subject matter described herein includes a system for determining an intravenous insulin infusion rate to correct hyperglycemia of a patient. FIG. 1 illustrates a block diagram of an exemplary system for determining an intravenous insulin infusion rate to correct hyperglycemia according to an embodiment of the subject matter disclosed herein. Referring to FIG. 1, system 100 includes a measurement receiver 102 configured to receive a glycemic measurement of a patient. For example, the glycemic measurement may be a measurement of blood glucose concentration of the patient. The glycemic measurement may be manually entered into receiver 102 via a computer user interface. Alternatively, the glycemic measurement may be electronically received by receiver 102. Receiver 102 may suitably process the glycemic measurement and pass data representative of the measurement to an insulin infusion rate calculator 104.

Insulin infusion rate calculator 104 is configured to estimate an insulin infusion maintenance rate for maintaining euglycemia of the patient. Calculator 104 may periodically or continuously calculate the maintenance rate based on a rate of change of blood glucose concentration of the patient and a previous rate of insulin infusion provided to the patient. In particular, calculator 104 may initially calculate an insulin infusion rate to maintain euglycemia based on provided patient condition data. The initial calculation of insulin infusion rate may then be output for use by a medical practitioner in administering insulin to the patient. Next, a glycemic response of the patient is measured while using the insulin infusion rate. The maintenance rate is re-estimated based on the glycemic response of the patient to the insulin infusion rate. The steps of determining an insulin infusion rate, measuring a glycemic response of the patient, and re-estimating the maintenance rate are repeatedly performed. The most recent estimate of insulin infusion maintenance is utilized to determine the following insulin infusion rate.

System 100 may include an insulin pump 106 and intravenous (IV) equipment 108. Insulin pump 106 may receive data from calculator 104 that indicates the insulin infusion rate to be administered to the patient. The insulin infusion rate may change in accordance with calculations performed by calculator 104. Insulin pump 106 provides insulin to IV equipment 108 in accordance with the insulin infusion rate. IV equipment 108 is suitably connected to the patient and pump 106 for intravenously providing insulin to the patient in accordance with the determined insulin infusion rate. The algorithm also has application in ambulatory medicine to the computation or testing of basal insulin infusion rates on a given fasting time interval during the 24-hr day for a patient using continuous subcutaneous infusion of insulin.

Figure 2:
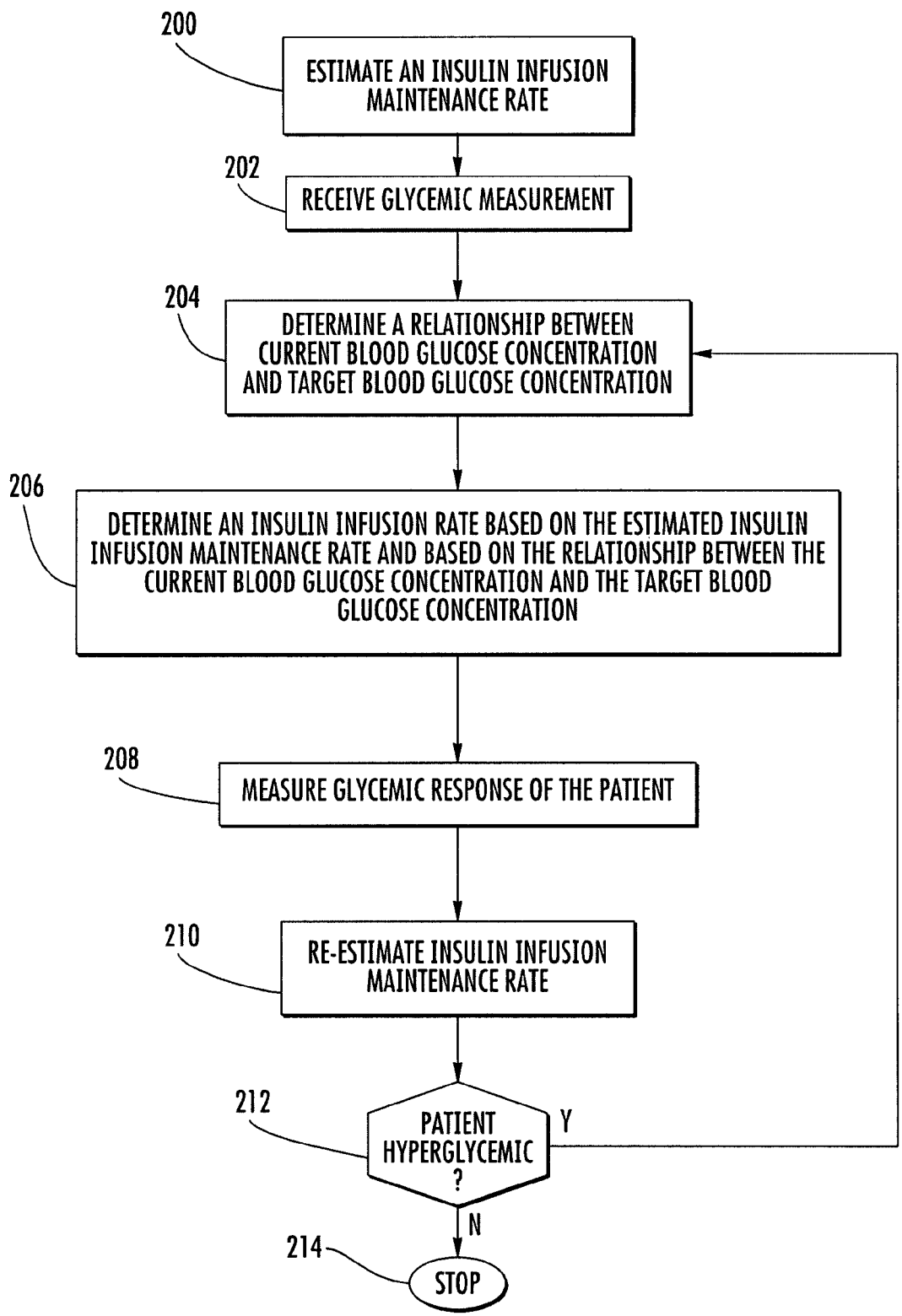
FIG. 2 is a flow chart of an exemplary process implemented by the system shown in FIG. 1 for determining an intravenous insulin infusion rate to correct hyperglycemia of a patient according to an embodiment of the subject matter disclosed herein.

FIG. 2 is a flow chart illustrating an exemplary process implemented by system 100 shown in FIG. 1 for determining an intravenous insulin infusion rate to correct hyperglycemia of a patient according to an embodiment of the subject matter disclosed herein. Referring to FIGS. 1 and 2, in block 200, calculator 102 estimates an insulin infusion maintenance rate to maintain euglycemia in a patient. The maintenance rate may initially be estimated based on patient condition. For example, the maintenance rate may be initially estimated based on patient condition data manually entered into receiver 102 via a computer user interface. In block 202, a glycemic measurement of the patient may be received by receiver 102. The glycemic measurements received by receiver may be representative of a current blood glucose concentration of the patient. Calculator 102 may include a timer for maintaining a record of times associated with the receipt of glycemic measurements.

After initially estimating a maintenance rate in block 200 and receiving a glycemic measurement in block 202, the process may include one or more iterations of blocks 204-212. In each iteration, an insulin infusion rate is determined and administered to the patient. The glycemic response of the patient to the administered insulin is measured, and the glycemic response used to re-estimate the maintenance rate. The estimated maintenance rate is used for the next iteration. The process may continue the iterations until hyperglycemia in the patient is corrected.

In block 204, calculator 104 determines a relationship between the current blood glucose concentration of the patient and a target blood glucose concentration. For example, calculator 104 may determine a distance of a current blood glucose concentration of the patient above a target blood glucose concentration.

Calculator 104 determines an insulin infusion rate based on the estimated insulin infusion maintenance rate and based on the relationship between the current blood glucose concentration of the patient and the target blood glucose concentration (block 206). In block 208, a glycemic response of the patient while using the insulin infusion rate determined in block 206 is measured. For example, after or during administration of insulin in accordance with block 206, receiver 102 may receive a glycemic measurement and communicate the measurement to calculator 104. In block 210, calculator 104 re-estimates the insulin infusion maintenance rate based on the glycemic response of the patient at a previous insulin infusion rate.

In block 212, calculator 104 may determine whether the patient is hyperglycemic. For example, based on a current glycemic measurement of the patient, calculator 104 may determine that a blood glucose concentration of the patient is within a target range for blood glucose concentration. If it is determined that the patient is hyperglycemic, the process may return to block 204 for beginning another iteration for correcting hyperglycemia of the patient. Otherwise, if it is determined that the patient is not hyperglycemic, the process may stop at block 214.

Figure 3:
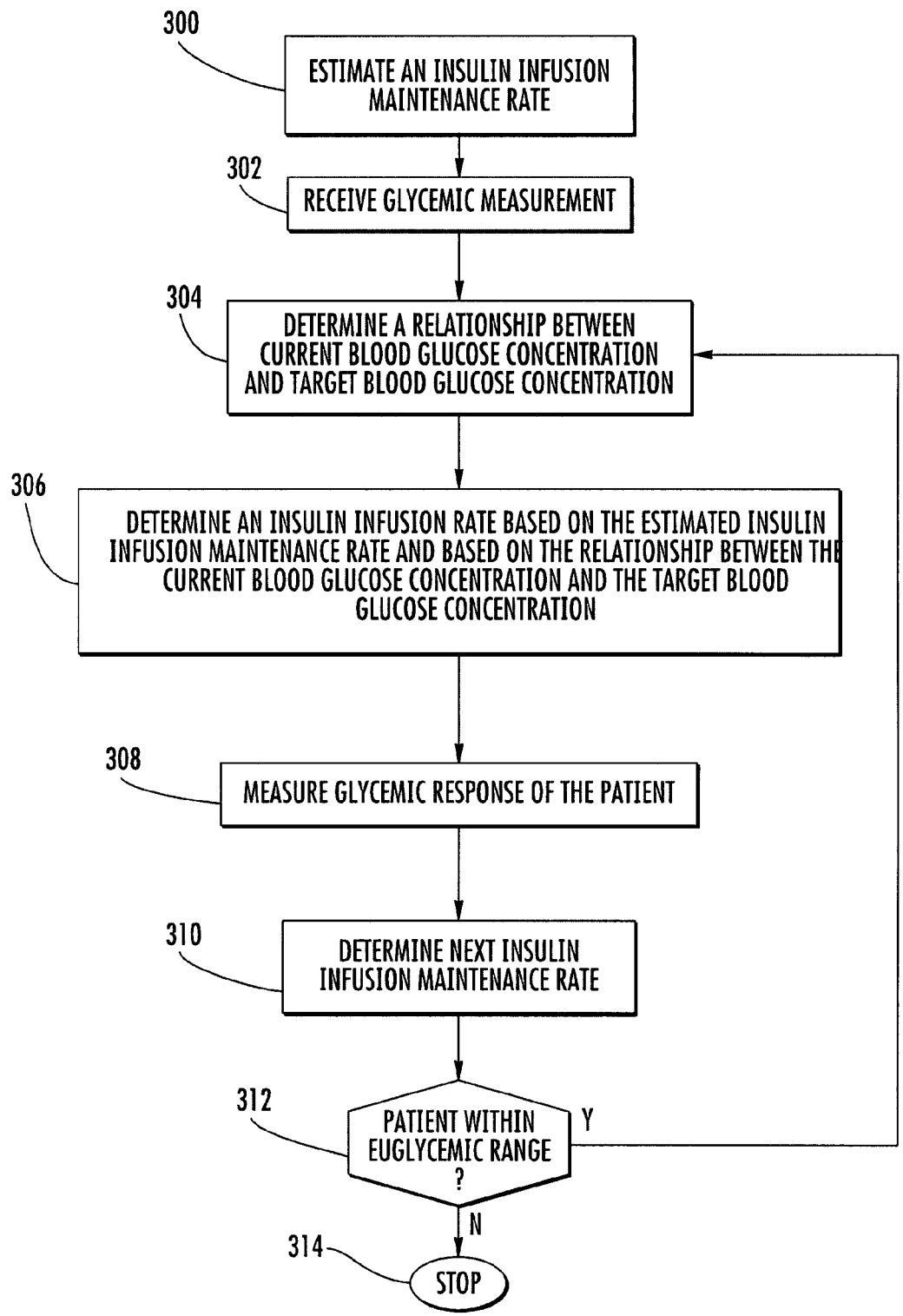
FIG. 3 is a flow chart of an exemplary process implemented by the system shown in FIG. 1 for determining an intravenous insulin infusion rate to maintain euglycemia of a patient according to an embodiment of the subject matter disclosed herein.

According to another aspect, system 100 may be configured to determine an intravenous insulin infusion rate to maintain euglycemia of a patient. FIG. 3 is a flow chart illustrating an exemplary process implemented by system 100 for determining an intravenous insulin infusion rate to maintain euglycemia of a patient according to an embodiment of the subject matter disclosed herein. Referring to FIGS. 1 and 3, in block 300, calculator 102 estimates an insulin infusion maintenance rate to maintain euglycemia in a patient. The maintenance rate may initially be estimated based on patient condition. In block 302, a glycemic measurement of the patient may be received by receiver 102.

After initially estimating a maintenance rate in block 300 and receiving a glycemic measurement in block 302, the process may include one or more iterations of blocks 304-312. In each iteration, an insulin infusion rate is determined and administered to the patient. The glycemic response of the patient to the administered insulin is measured. An insulin infusion maintenance rate for a next iteration is determined by (1) re-estimating the insulin infusion maintenance rate based on the glycemic response of the patient at a previous insulin infusion rate; (2) carrying forward a previous insulin infusion maintenance rate unchanged to become the next insulin infusion maintenance rate; or (3) based on criteria for risk of hypoglycemia setting the next insulin infusion maintenance rate to be a percentage less than the previous insulin infusion maintenance rate. The determined maintenance rate is used for the next iteration. The process may continue the iterations for maintaining euglycemia of the patient.

In block 304, calculator 104 determines a relationship between the current blood glucose concentration of the patient and a target blood glucose concentration. For example, calculator 104 may determine a distance of a current blood glucose concentration of the patient above a target blood glucose concentration.

In block 306, calculator 104 determines an insulin infusion rate based on the estimated insulin infusion maintenance rate and based on the relationship between the current blood glucose concentration of the patient and the target blood glucose concentration. A glycemic response of the patient while using the insulin infusion rate determined in block 306 is measured (block 308). For example, after or during administration of insulin in accordance with block 206, receiver 102 may receive a glycemic measurement and communicate the measurement to calculator 104.

In block 310, calculator 104 determines a next insulin infusion maintenance rate for a next iteration. The determination of the next insulin infusion maintenance rate may include one of (1) re-estimating the insulin infusion maintenance rate based on the glycemic response of the patient at a previous insulin infusion rate; (2) carrying forward a previous insulin infusion maintenance rate unchanged to become the next insulin infusion maintenance rate; or (3) based on criteria for risk of hypoglycemia setting the next insulin infusion maintenance rate to be a percentage less than the previous insulin infusion maintenance rate. As described in further detail herein, the maintenance rate may be determined based on percentage techniques for re-estimating of the maintenance rate in a euglycemic target range. The maintenance rate may be carried forward if a previous blood glucose concentration of the patient is less than a target blood glucose concentration.

In block 312, calculator 104 may determine whether the patient is within the euglycemic range. For example, based on a current glycemic measurement of the patient, calculator 104 may determine that a blood glucose concentration of the patient is within a target range for euglycemia. If it is determined that the patient is within a target range for euglycemia, the process may return to block 304 for beginning another iteration for maintaining euglycemia. Otherwise, if it is determined that the patient is not within the range for euglycemia, the process may stop at block 314. Further, if it is determined that the patient is not within the range for euglycemia, other processes in accordance with the subject matter disclosed herein may be applied for determining an infusion rate based on whether the patient is hypoglycemic or hyperglycemic.

Figure 4:
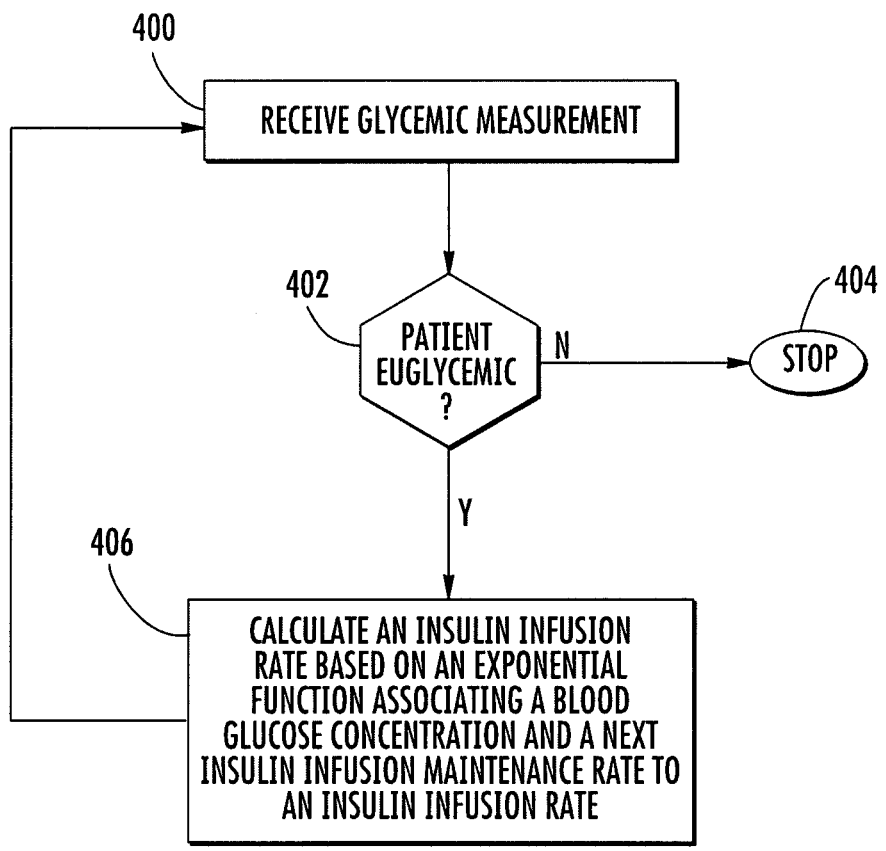
FIG. 4 is a flow chart of an exemplary process implemented by the system shown in FIG. 1 for determining an intravenous insulin infusion rate to prevent hypoglycemia of a patient according to an embodiment of the subject matter disclosed herein.

According to another aspect, system 100 may be configured to determine an intravenous insulin infusion rate to prevent hypoglycemia of a patient. FIG. 4 is a flow chart illustrating an exemplary process implemented by system 100 for determining an intravenous insulin infusion rate to prevent hypoglycemia of a patient according to an embodiment of the subject matter disclosed herein. Referring to FIGS. 1 and 4, in block 400, receiver 102 receives a glycemic measurement of the patient. Calculator 104 determines whether a blood glucose concentration of the patient is within a euglycemic range (e.g., a nonhypoglycemic and a nonhyperglycemic range) (block 402). For example, calculator 104 may compare the glycemic measurement of the patient to stored data indicating a euglycemic range for determining whether the blood glucose concentration of the patient is within the range. If it is determined that the patient is not within the euglycemic range, the process may stop at block 404.

In response to determining that the blood glucose concentration of the patient is within the euglycemic range, calculator 104 calculates an insulin infusion rate based on an exponential function associating a blood glucose concentration and a next insulin infusion maintenance rate to an insulin infusion rate (block 406). A more detailed description of the calculation is provided below. Insulin may be administered to the patient based on the calculated insulin infusion rate.

The process returns to block 400 for receiving another glycemic measurement of the patient. Further, the process may continue for another iteration through block 406 if it is determined that the patient is euglycemic in block 402.

Program Input and Output

Calculations after each hyperglycemic iteration of the algorithm use the rate of change of blood glucose concentration ($ROD_{previous}$) and the previous infusion rate of insulin ($IR_{previous}$) to estimate the MR necessary to preserve euglycemia. In order to reassign the MR for the next iteration, the algorithm chooses between the mathematical re-estimation of $MR_{csne}$, the previous MR carried forward, or modifications of MR based on clinical input data.

The model defines the therapeutically ideal rate of change of blood glucose concentration (BG) for future time to be dependent upon the current BG ($BG_{current}$) and certain parameters of the algorithm. The therapeutically ideal rate of descent ($ROD_{ideal,next}$) for BG above upper target, or rate of ascent ($ROA_{ideal,next}$) for BG below true target, are treated as two different intermediary variables. The algorithm may include the ideal rate of change for BG, the MR, and $BG_{current}$ to define the next insulin infusion rate ($IR_{next}$). For patients not at target, the algorithm predicts the time course of glycemic response.

Input to the algorithm may include $BG_{previous}$, $testtime_{previous}$, $BG_{current}$, $testtime_{current}$, and $IR_{previous}$. The computer memory may provide the first two pieces of input. $BG_{previous}$ represents BG at the beginning of the iteration just completed. $BG_{current}$ represents the current BG. $\Delta time_{previous}$ represents the duration of the previous iteration (i.e. $testtime_{current} - testtime_{previous}$).

The output of the algorithm may include $IR_{next}$ and testtime$_{next}$. In computing the output, intermediary variables may be used. The previous rate of change of BG may be given in mg/dL per hour.

The observed rate of descent ($ROD_{previous}$ having a value of 0 except within the hyperglycemic range) and rate of ascent ($ROA_{previous}$ having a value of 0 except when the blood glucose concentration is below a target blood glucose concentration range) may be treated as different variables. Each variable may assume values that are positive, zero, or negative during observation of previous measurements. Equations for $ROD_{previous}$ and $ROA_{previous}$ follow:

$$ROD_{previous} = \frac{BG_{previous} - BG_{current}}{\Delta time_{previous}}, \text{ for } BG_{previous} \geq BG_{true\ target}$$

$$ROD_{previous} = 0, \text{ for } BG_{previous} < BG_{true\ target}$$

$$ROA_{previous} = \frac{BG_{current} - BG_{previous}}{\Delta time_{previous}}, \text{ for}$$

$$BG_{previous} < BG_{true\ target}$$

$$ROA_{previous} = 0, \text{ for } BG_{previous} \geq BG_{true\ target}$$

In equations that define the next insulin infusion rate ($IR_{next}$) provided herein below, the $ROD_{ideal,next}$ and $ROA_{ideal,next}$ appear and may be treated as different intermediary variables, each having positive or negative values. Equations for $ROD_{ideal,next}$ and $ROA_{ideal,next}$ follow:

$ROD_{ideal,next}$ calculated, videinfra, for $BG_{previous} \geq BG_{upper\ target}$ $ROD_{ideal,next} = 0$, for $BG_{previous} < BG_{upper\ target}$ $ROA_{ideal,next}$ calculated, videinfra, for $BG_{previous} < BG_{true\ target}$ $ROA_{ideal,next} = 0$, for $BG_{previous} \geq BG_{true\ target}$

Ideal Future Rate of Change of BG During Hyperglycemia

In future time, at a given $BG_{current} \geq BG_{upper\ target}$, the $ROD_{ideal,next}$ is user-definable, but the algorithm will calculate a BG-dependent default value according to a linear rule or an negative exponential asymptotic rule.

During hyperglycemia, according to the linear rule the $ROD_{ideal,next}$ decreases linearly from a defined ROD ($ROD_{@BGcritical\ high}$) at the critical high BG ($BG_{critical\ high}$) to $ROD_{ideal,next}$=zero at upper target BG ($BG_{upper\ target}$), and increases linearly to a conservatively assigned maximum rate ($ROD_{max}$), 70 mg/dL per hour. If the BG declines at rates higher than $ROD_{max}$, non-insulin mediated mechanisms may be responsible, such as rehydration.

The following two given points may define the linear function (BG, $ROD_{ideal,next}$): (1) $BG_{upper\ target}$ (zero); and $BG_{critical\ high}$ ($ROD_{@BGcritical\ high}$). The following equation defines $ROD_{ideal,next}$ for $BG_{current} \geq BG_{upper\ target}$ (iteration number n>1):

$$ROD_{ideal,next} = ROD_{@BG\ critical\ high} * \frac{BG_{current} - BG_{upper\ target}}{BG_{critical\ high} - BG_{upper\ target}}$$

When the equation for $ROD_{ideal,next}$ gives a value higher than $ROD_{max}$, the value of $ROD_{max}$ may be substituted. A more aggressive rule for assigning $ROD_{ideal,next}$ may be used for iteration n=1 (vide infra).

During hyperglycemia, according to the negative exponential asymptotic rule, the $ROD_{ideal,next}$ approaches the $ROD_{max}$ as an asymptote. A negative exponential function defines $ROD_{ideal,next}$ for $BGcurrent \geq BG_{upper\ target}$:

$$ROD_{ideal,next} = ROD_{ideal,next,max} *$$
$$\left\{ 1 - e^{[-(BGcurrent-BGuppertarget)/(BGcriticalhigh-BGuppertarget)]* \atop ln[(RODideal,next,max)/(RODideal,next,max-ROD@BGcriticalhigh)]} \right\}$$

("minus negative exponent" asymptote technique)

The equations for the linear function and for the "minus negative exponent" technique may be written in shorthand by defining the fractional elevation of BG relative to critical high (FEBG) by the following equation:

FEBG relative to critical high=($BG_{current}$-$BG_{uppertarget}$)/($BG_{criticalhigh}$-$BG_{uppertarget}$) for $BG \geq BG_{upper\ target}$ The Linear Equation is Shown as:

$ROD_{ideal,next}$=$ROD_{@BGcritical\ high}$*FEBG

The minus negative exponent technique is shown as:

$$ROD_{ideal,next} = ROD_{ideal,next,max} *$$
$$\{1 - e^{-FEBG*ln[(RODideal,next,max)/(RODideal,next,max-ROD@BGcriticalhigh)]}\}$$

Ideal Future Rate of Change of BG During Euglycemia

At a given $BG < BG_{true\ target}$, the ideal ROA is defined under the model that a maximum rate of ascent ($ROA_{max}$) exists in nature at BG=70 mg/dL for each patient. It is undesirable for the observed ROA to equal the $ROA_{max}$ at every euglycemic BG. The algorithm states that for $BG < BG_{true\ target}$, the ideal value of ROA is linearly and negatively related to the fractional completeness of ascent of BG, declining from $ROA_{max}$ at BG 70 mg/dL to ROA=zero at $BG_{true\ target}$.

Two given points may define the linear function (1) 70 mg/dL, $ROA_{max}$; and (2) $BG_{true\ target}$ (zero). The following equation defines $ROA_{ideal}$ for $BG < BG_{true\ target}$:

$$ROA_{ideal} = ROA_{max} * \frac{BG_{true\ target} - BG}{BG_{true\ target} - 70\ mg/dL}$$

If the ideal ROA ($ROA_{ideal}$) is achieved, then the value of fractional reduction of $ROA_{ideal}$ to less than $ROA_{max}$ (FR-ROA) is the same as the value of the fractional completeness of ascent of BG (FCABG). The following equations define the fractional reduction of $ROA_{ideal}$ and the fractional completeness of ascent of BG at different BG:

fractional reduction of $ROA_{ideal}$=($ROA_{max}$-$ROA_{ideal}$)/$ROA_{max}$), for 70 mg/dL $\leq$ BG < $BG_{true\ target}$ fractional reduction of $ROA_{ideal}$=0, for $BG \geq BG_{true\ target}$ fractional completeness of ascent of BG=(BG−70 mg/dL)/($BG_{true\ target}$−70 mg/dL), for 70 mg/dL≤BG<$BG_{true\ target}$ fractional completeness of ascent of BG=1, for BG≥$BG_{true\ target}$ The equivalence of FRROA and FCABG are provided by the following equations:

($ROA_{max}$−$ROA_{ideal}$)/$ROA_{max}$=(BG−70 mg/dL)/ ($BG_{true\ target}$−70 mg/dL), for BG<$BG_{true\ target}$

FRROA=FCABG

The algorithm provides that after hypoglycemia (<BG 70 mg/dL), the value of $BG_{current}$ is reassigned equal 70 mg/dL ($BG_{current,revised}$) even if treatment of hypoglycemia has resulted in a higher subsequent value. If no hypoglycemia occurred, then $BG_{current,revised}$=$BG_{current}$. The following equation defines $ROA_{ideal,next}$ for $BG_{current}$<$BG_{true\ target}$:

$$ROA_{ideal,next} = ROA_{max} * \frac{BG_{true\ target} - BG_{current,revised}}{BG_{true\ target} - 70\ mg/dL}$$

Ideal Rate of Change of Blood Glucose (BG)

There is no patient-dependent determinant of the ideal rate of descent of BG (ROD). Rather, the ideal ROD is determined by the ambient BG, taken together with patient-independent user-defined algorithm parameters. In contrast, in both past time and future time, a patient-dependent algorithm parameter, specifically $ROA_{max}$, determines the ideal rate of ascent of blood glucose, when considered together with the current BG and the user-defined $BG_{true\ target}$.

Figure 5:
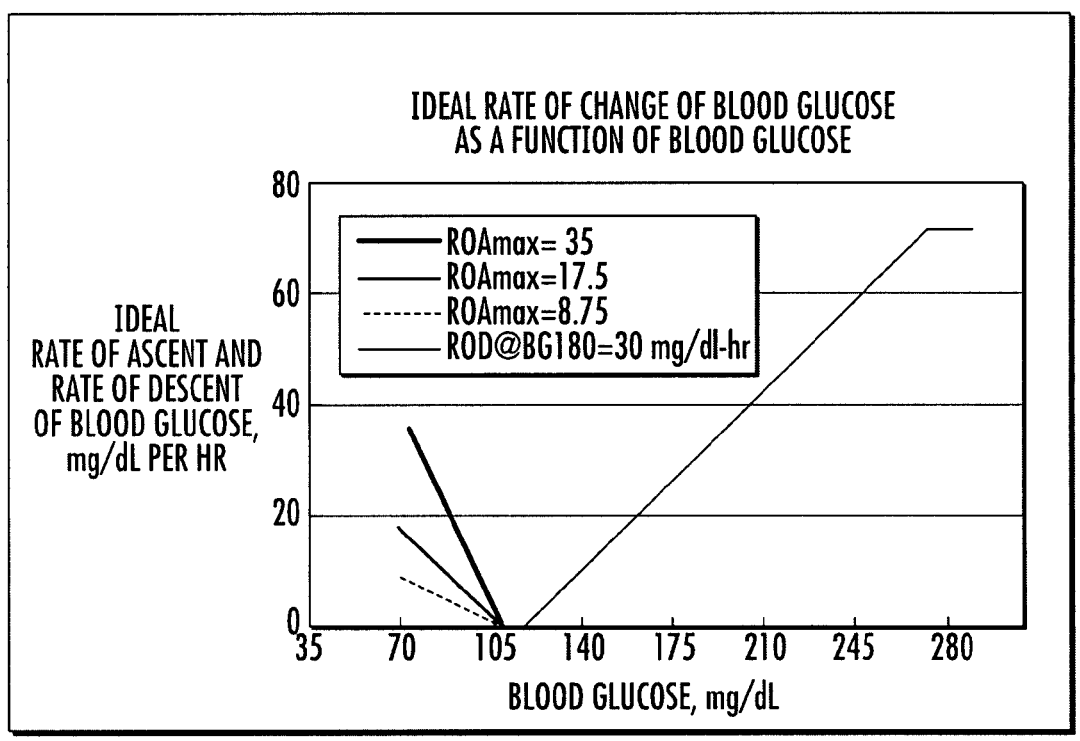
FIG. 5 is a graph of ideal rates of change of blood glucose concentration according to an embodiment of the subject matter disclosed herein.

FIG. 5 is a graph of ideal rates of change of blood glucose concentration. Referring to FIG. 5, for BG<105 mg/dL, the ideal future rate of ascent of blood glucose is shown using the default value of $BG_{true\ target}$=105 mg/dL for patients having $ROA_{max}$=35, 17.5 or 8.75 mg/dL. For BG≥110 mg/dL, the ideal rate of descent is shown using the default values of $BG_{upper\ target}$=110 mg/dL, $BG_{critical\ high}$=180 mg/dL, $ROD_{@BGcritical\ high}$=30 mg/dL, and $ROD_{max}$=70 mg/dL.

Future BG Prediction and Time-to-Target

For the purposes of this section, it is assumed that the ideal rate of change of BG is actually achieved after determination of $BG_{current}$. If no action is taken to restate the $ROD_{ideal,next}$, $ROA_{ideal,next}$ or revise the IR, then the future BG ($BG_{future}$) as a function of Δ time and the time-to-target are uniquely future, determined.

Future BG Prediction and Time-to-Target During Hyperglycemia with Constant ROD During descent of BG, assuming $ROD_{ideal,next}$≤$ROD_{max}$, and assuming no subsequent revision to IR or ROD occurs, then for any hyperglycemic $BG_{current}$ the following equations may apply:

$BG_{future}$=$BG_{current}$−$ROD_{ideal,next}$*Δtime time-to-target=($BG_{critical\ high}$−$BG_{upper\ target}$)/ $ROD_{@BG\ critical\ high}$ During hyperglycemia with BG>$BG_{upper\ target}$, the ROD determines time to upper target. For the default parameter values ROD=30 mg/dL per hour at BG 180 mg/dL and $BG_{upper\ target}$=105 mg/dL, the time-to-target would be 2.5 hours if $ROD_{ideal,next}$ were met. In actual practice, during progressive correction of hyperglycemia and prior to attainment of target range control, as a safety precaution, the caregiver uses hourly monitoring of blood glucose to determine the need for downward revisions of $ROD_{ideal,next}$ and $IR_{next}$. At the time of each new BG measurement, the correction rate (CR) is reassigned. If the linear rule is used for assignment of $ROD_{ideal,next}$, then for ROD<$ROD_{max}$, the projected time-to-target should remain the same after each reassignment of CR, such that the start time for time-to-target is reset to 2.5 hours every time the CR is reset. Generally, because of the deliberate IR reductions, the time-to-target is longer than the time that would have been calculated (theoretically infinite) such that is would be more appropriate to speak time half way to target. In fact, even if the model were completely accurate, attainment of the $ROD_{ideal,next}$ would occur only if MR had been correctly discovered.

Future BG Prediction and Time-to-Target During Euglycemia with Constant ROA

During euglycemia with BG<$BG_{true\ target}$, if the negative linear relation between ROA and BG is achieved by the use of appropriate insulin therapy under algorithm, then for a given patient, under given conditions of illness, carbohydrate exposure and concomitant therapies, the $ROA_{max}$ uniquely determines a specific time-to-target not only at BG=70 mg/dL but also determines the same time-to-target at any euglycemic BG<$BG_{true\ target}$. At any euglycemic BG, the ROAmax determines the time-to-target as defined by the following equation:

time-to-target = ($BGtrue\ target$ − 70 mg/dL) / $ROA_{max}$

= ($BGtrue\ target$ − $BG_{current}$) / $ROA_{ideal}$

During ascent of BG, assuming no revision to ROA occurs, then for any euglycemic $BG_{current}$ the following equation defines $BG_{future}$:

$BG_{future}$=$BG_{current}$+$ROA_{ideal,next}$*Δtime

In actual practice, during ascent of BG on the euglycemic range, the time-to-target may elapse before the next test time has occurred, which may be about 2 hours. Thus, overshoot is seen such that the next BG exceeds $BG_{true\ target}$. The default assumption is that $ROA_{max}$ is 17.5 mg/dL per hour and, if the restraining rate of insulin has been assigned at the previous test time, the time-to-target is 2 hours for any euglycemic BG<$BG_{true\ target}$. Recurring episodes of unexplained overshoot point to the possibility that the default $ROA_{max}$ does not fit the patient. Reassignment of individual $ROA_{max}$ may occur as a result of observations made during treatment.

Parameters of the Model: $MR_{true}$, $ROA_{max}$, and G-per-Diem

Having a model to predict response to therapy is an essential improvement over making arbitrary percentage-based reactive insulin rate adjustments. It is expected that use of a well-honed model may allow a medical practitioner to come closer to exact targeting of the desired blood glucose results, with reduction of glycemic variability and hypoglycemia.

The model uses parameters that are either given as defaults or user-definable. These user-definable parameters may include $ROD_{ideal\ max}$, $ROD_{ideal}$ at $BG_{critical\ high}$, $BG_{true\ target}$, $BG_{upper\ target}$, $BG_{lower\ target}$, $IR_{@BG70}$, $MR_{initial}$, and other suitable parameters. The model in accordance with the subject matter described herein utilizes three parameters that are not user-definable, but are discoverable or estimable as population averages or as individual patient characteristics. These parameters are $MR_{true}$, $ROA_{max}$, and G-per-Diem. Default values for $MR_{true}$, $ROA_{max}$, and G-per-Diem may be used with several possible population values for initial estimation of $MR_{true}$, 1800 mg/dL for G-per-Diem, and 17.5 mg/dL per hour for $ROA_{max}$. Refined estimations of the values of the three algorithm parameters are identifiable by measurements and calculations that can be obtained in the course of clinical practice.

$MR_{true}$ is a maintenance requirement that each treated patient is assumed to have for exogenous insulin. Further, $MR_{true}$ may be referred to as the mean IR on stable intervals ($IR_{mean,stable\ interval}$).

$ROA_{max}$ is the maximum rate of ascent of BG that can occur spontaneously during euglycemia. Further, $ROA_{max}$ is defined as the rate of ascent (ROA) that occurs at the boundary between euglycemia and hypoglycemia, during negligible insulin infusion, in the absence of counterregulatory response to hypoglycemia. The blood glucose value at which these criteria are met is assumed to be 70 mg/dL. Under given conditions of illness, carbohydrate exposure, and concomitant therapies, $ROA_{max}$ is assumed to be a discoverable constant characteristic of the patient under given conditions of care, and is independent of insulin therapy, insulin secretory capacity or insulin resistance. The $ROA_{max}$ depends upon ambient conditions affecting glucose appearance rate, specifically the rate of carbohydrate exposure (C6R) and the maximum rate of hepatic glucose output ($HGO_{max}$) during non-hypoglycemia.

The ROA should equal the ROAmax only at the boundary between euglycemia and hypoglycemia but otherwise, at higher BG concentration, the ROA should be less than $ROA_{max}$. For patients known to require maintenance amounts of insulin under given conditions of illness, carbohydrate exposure and concomitant therapies, the algorithm may make the simplified assumption that at any euglycemic BG>70 mg/dL, the same rate of ascent (ROA) of BG would occur that occurs at BG=70 mg/dL, and on the euglycemic range the same ROA would be sustained, i.e. the $ROA_{max}$ would be sustained as BG rises, unless more insulin is provided. If negligible insulin is delivered at BG 70 mg/dL, the $ROA_{max}$ determines the time-to-target that would be observed during ascent of BG.

At any given euglycemic BG>70 mg/dL, assuming the insulin infusion achieves the desired results, it is predicted that the value of ROA has an identical value for every patient who shares the same $ROA_{max}$, i.e. the value of ROA is $ROA_{ideal}$ (see FIG. 5 for example). The predicted rate of ascent in response to insulin therapy during euglycemia is defined by the following equation that relates the $ROA_{max}$ parameter to the restraining rate of insulin infusion necessary for attainment of $ROA_{ideal}$:

ROAideal=$ROA_{max}$*(ln MR−ln IR)/(ln MR−ln $IR_{@BG70}$)

Figure 6:
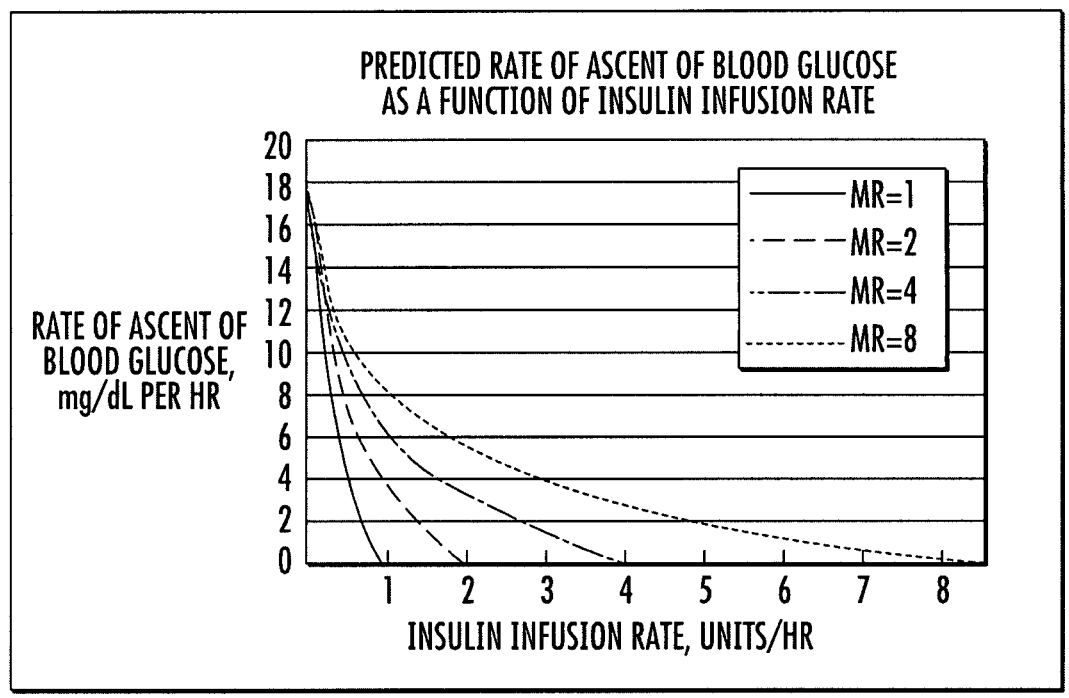
FIG. 6 is a graph of the predicted rate of ascent at a given maximum rate of ascent of blood glucose ($ROA_{max}$)=17.5 mg/dL per hr in response to insulin therapy during euglycemia appropriate to achieve ideal rate of ascent with iso-maintenance rate curves according to an embodiment of the subject matter disclosed herein.

FIG. 6 is a graph of the predicted rate of ascent in response to insulin therapy during euglycemia appropriate to achieve $ROA_{ideal}$. For BG<$BG_{true\ target}$, the $IR_{next}$ is assigned to be less than MR. At BG=70 mg/dL, $IR_{next}$ is assigned the value of $IR_{@BG70}$, a negligible infusion rate of insulin, at which the patient-specific $ROA_{max}$ occurs. The predicted value of the ROA is a logarithmically declining function of the assigned $IR_{next}$. During the ensuing time interval, after assignment of $IR_{next}$ and until $BG_{true\ target}$ is reached, the ROA will have a constant value. FIG. 6 shows a patient having known $ROA_{max}$=17.5 mg/dL per hour.

G-per-Diem is referred to as insulin-mediated BG disposal per kg body weight in response to total daily dose of exogenously administered insulin, if expressed in gm/K, or, if divided by total daily dose of insulin and expressed in mg/dL, the parameter is conceived of as insulin-mediated drop of BG concentration in response to one unit of insulin. The following equation relates the G-per-Diem parameter to insulin dose and glycemic response:

$$\frac{G\text{-per-Diem}}{\text{total daily dose of insulin}} = \frac{\text{drop of } BG}{1 \text{ unit insulin}}$$

The acronym for G-per-Diem is taken from the concept of "glucose flux per daily dose of insulin, exogenously mediated". The parameter has a population average often estimated at 1500 mg/dL, 1800 mg/dL, or 1720 mg/dL. The parameter value is considered to be independent of insulin resistance or body weight but dependent upon carbohydrate exposure and endogenous insulin effect. Historically, the G-per-Diem parameter was created to assist in making subcutaneous insulin dose decisions that would apply to future time. Under the algorithm, the G-per-Diem parameter is used together with MR and $BG_{current}$ during hyperglycemia to determine a correction rate of insulin infusion (CR). If applied to past time, the G-per-Diem parameter also may be viewed as a constant that permits fractional apportionment of $IR_{previous}$, delivered during hyperglycemia, between the putative correction rate of insulin infusion (CR) and the MR.

The following equation relates the G-per-Diem parameter to insulin infusion rate for correction of hyperglycemia and the rate of descent of BG:

$$\frac{G\text{-per-Diem}}{MR * 24 \text{ hours}} = \frac{ROD}{CR}$$

Figure 7:
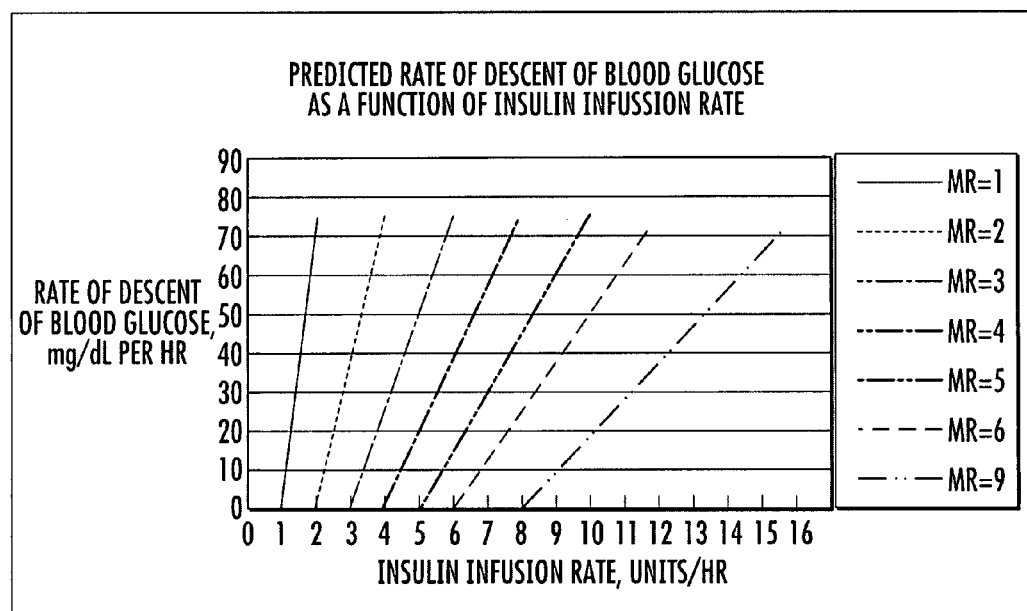
FIG. 7 is a graph of a predicted rate of descent of blood glucose concentration in response to insulin therapy during hyperglycemia with iso-maintenance rate curves according to an embodiment of the subject matter disclosed herein.

FIG. 7 is a graph of a predicted rate of descent of blood glucose concentration in response to insulin therapy during hyperglycemia. The predicted rate of descent is defined by the following equation:

$$ROD_{ideal,next} = CR * \frac{G\text{-per-Diem}}{24 \text{ hours} * MR}$$

Values for $ROD_{ideal,next}$ are restricted to be ≤70 mg/dL per hour except for diabetic ketoacidosis and hyperglycemic hyperosmolar state, for which values for $ROD_{ideal,next}$ are 150 mg/dL per hour. For BG>$BG_{true\ target}$, the $IR_{next}$ is assigned to be greater than MR. The ROD in future time is predicted under the model as a linear function of the assigned $IR_{next}$.

Physiological Determinants of Algorithm Parameters

A model in accordance with the subject matter described herein does not require compartment analysis or direct knowledge of determinants of the values of algorithm parameters such as insulin secretory capacity or insulin resistance. Estimates of the $ROA_{max}$, G-per-Diem and $MR_{true}$ are discoverable or calculable as the result of observations made in the course of routine clinical care.

Table 1 below shows putative determinants of the value of principal parameters of the algorithm that are discoverable in nature and are not user-defined.

TABLE 1

Putative Determinants of Parameter Values

| Parameter | Units of Measure | C6R and $HGO_{max}$ | Endogenous Insulin Production | Peripheral and Hepatic Insulin Resistance | Body Weight |
|---|---|---|---|---|---|
| ROAmax | mg/dL per hour | + | 0 | 0 | 0 |
| G-per-Diem | mg/dL | + | + | 0 | 0 |
| MR/kg | units/hour per kg | + | + | + | 0 |
| MR | units/hour | + | + | + | + |

$ROA_{max}$ is the nonhypoglycemic maximum rate of ascent of blood glucose during negligible insulin infusion. G-per-Diem is the glucose flux per daily dose of insulin, exogenously mediated. MR is the maintenance rate of insulin infusion. C6R is the ambient rate of infusion of carbohydrate per hour. $HGO_{max}$ is maximum hepatic glucose output during negligible insulin infusion under nonhypoglycemic ambient conditions. Default values may be population-specific. For example, after study, it may be determinable that a patient receiving maintenance carbohydrate with type 1 diabetes may be assigned G-per-Diem 1800 mg/dL but with type 2 diabetes 900 mg/dL.

Default Values for Algorithm Parameters

The algorithm may be piloted using conservative assumptions about default values for algorithm parameters, taken from the publication "Performance of a Dose-Defining Insulin Infusion Protocol Among Trauma Service Intensive Care Unit Admission," by Braithwaite et al., *Diabetes Technol. Ther.*, 8 (4): pp. 476-88, the disclosure of which is incorporated by reference in its entirety. Revision of MR may commence after the first iteration of every patient treatment course may be set to 1800 mg/dL for G-per-Diem, 17.5 mg/dL per hour for $ROA_{max}$, and 2 units per hour for $MR_{true}$ (where revision commences after the first iteration). $IR_{@BG70}$ is the negligible insulin infusion rate used at BG 70 mg/dL. The default values for $IR_{@BG70}$ are 0.1 units/hour for adults, 0.002 units/kg per hour for children (alternatively, insulin infusion is turned off until test $time_{next}$, if the calculated rate is below the minimum delivery capability of the syringe pump.

Notation for Indexing of Iterations and of the Data from Iterations, from 0 to n Each patient treatment course has a unique identifier number, the "patient treatment course" number, for use in indexing. Within a given indexed patient treatment course, each iteration of the algorithm is given a sequentially assigned "iteration number," used for indexing. The initial iteration is given iteration number="1," and each iteration thereafter is numbered sequentially from "1" to "n". For the iteration just completed, the index number is "n". For iteration about to start, the index number is "n+1".

Input data for iteration (1) are labeled as follows:
$Testtime_{current}(0)$
$BG_{current}(0)$
$BG_{current,rev}(0)$
$MR_{csne,revised}(0)$, otherwise known as MRinitial
$ROD_{ideal,next}(0)$
$ROA_{ideal,next}(0)$
$IR_{next}(0)$ At the time of making calculations that are dependent upon completion of an iteration, the index number of the iteration "n" is assigned, all point-of-care data, all variables derived from the iteration just completed, and all advice given from the next iteration are now given the index number of concluded iteration "n" as follows:
$BG_{previous}(n)$
$BG_{previous,revised}(n)$
$BG_{current}(n)$
$BG_{current,rev}(n)$
$testtime_{previous}(n)$
$testtime_{current}(n)$
$time_{previous}(n)$
$ROD_{previous}(n)$
$ROD_{previous,revised}(n)$
$ROA_{previous}(n)$
$ROA_{previous,revised}(n)$
$IR_{previous}(n)$
$MR_{csne}(n)$
$MR_{csne,revised}(n)$
$ROD_{ideal,next}(n)$
$ROA_{ideal,next}(n)$
$IR_{next}(n)$
$testtime_{next}(n)$ For the iteration "n+1" about to start, for which $IR_{next}(n)$ must be calculated, the index number is "n+1". The equation for $IR_{next}(n)$, for the coming iteration "n+1," should include input of data above, labeled as belonging to the iteration "n". $MR_{csne,revised}(n)$ from iteration "n" is used as MR (n) in the calculation of $IR_{next}$ for iteration "n+1". Insulin at the rate of $IR_{next}(n)$, calculated upon completion of iteration "n," is infused at this rate for the duration of iteration "n+1". At the time of completion of iteration "n," the $ROA_{ideal,next}(n)$ is the rate of ascent that is hoped for in iteration "n+1". At the time of completion of iteration "n," the $ROD_{ideal,next}(n)$ is the rate of descent that is hoped for in iteration "n+1".

Upon completion of the iteration "n+1," some information acquires a second index number and is stored redundantly in a program file under each of the two index numbers. $testtime_{current}(n)$ becomes $testtime_{previous}(n+1)$. $BG_{current}(n)$ becomes $BG_{previous}(n+1)$. $BG_{current,revised}(n)$ becomes $BG_{previous,revised}(n+1)$.

At the end of iteration (n+1), the timer of the insulin infusion rate calculator may assign $testtime_{current}(n+1)$, rounding to the nearest algorithm time. At the end of iteration (n+1), a medical practitioner may be queried on the value of $BG_{current}$ and $IR_{previous}$. If no reassignment of IR has occurred by the medical practitioner during iteration (n+1), $IR_{next}(n)$ becomes $IR_{previous}(n+1)$. If there has been a reassignment of IR by the medical practitioner during iteration (n+1), $IR_{previous}(n+1)$ assumes the value entered by the medical practitioner. If it is necessary by BG criteria to carry forward the last $MR_{csne,revised}$ rather than recalculate $MR_{csne}$, then $MR_{csne,revised}(n)$ becomes $MR_{csne}(n+1)$ and the specific value is stored redundantly in two places, each place having the appropriate index number. Upon completion of the iteration "n+1," the rate of change of BG may differ from what was desired: (1) prior to starting iteration "n+1," $ROA_{ideal,next}(n)$ or $ROD_{ideal,next}$ (n) were planned for; and (2) $ROD_{previous}$ (n+1) or $ROA_{previous}$ (n+1) are likely to differ from what had been planned.

Equations of the Algorithm Relating Insulin and BG Under the Model

Figure 8:
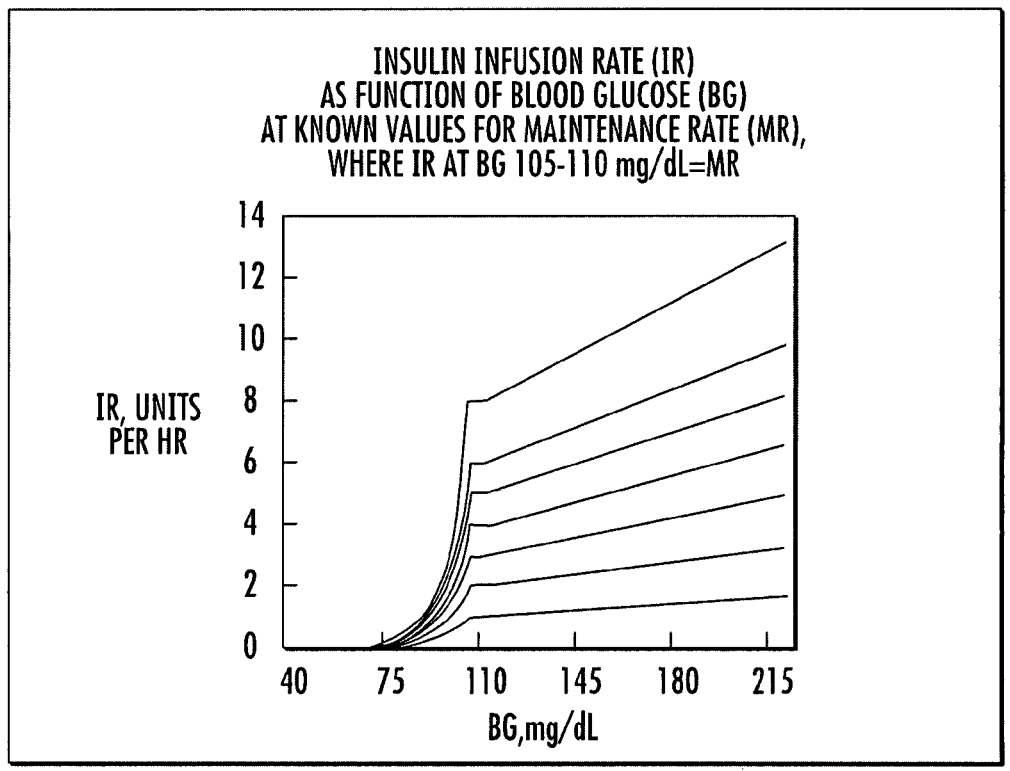
FIG. 8 is a graph representing an exemplary equation of the algorithm for relating an insulin infusion rate to blood glucose concentration with iso-maintenance rate curves according to an embodiment of the subject matter disclosed herein.

FIG. 8 is a graph representing an exemplary equation of the algorithm for relating an insulin infusion rate to blood glucose concentration. Referring to FIG. 8, a family of iso-MR curves for several different MR values is shown. The equation for insulin infusion rate as a function of BG is graphed from known values of MR. The shown MR values are 1, 2, 3, 4, 5, 6, and 8 units per hour.

For patients having maintenance requirement for exogenous insulin such that $MR > IR_{@BG70}$, the previous rate of change of BG is captured by computation of the MR. The ideal future rate of change of BG is engineered through the assignment of either the restraining rate of insulin infusion necessary to achieve the ideal FRROA (during euglycemia), or the CR (during hyperglycemia). Therefore, a relationship is stated between insulin infusion rate and rate of change of BG by either of the following equivalent equations for the algorithm in past or future time:

$$IR = IR_{@BG70} * \left(\frac{MR}{IR_{@BG70}}\right)^{\text{"fractional completeness of ascent of BG"}} + CR(\text{if any})$$

$$IR = IR_{@BG70} * \left(\frac{MR}{IR_{@BG70}}\right)^{\text{"fractional reduction of ROAideal to less than ROA max"}} + CR(\text{if any})$$

where MR is the maintenance rate of insulin infusion, CR is the correction rate for hyperglycemia (a linear function of MR and BG, non-zero only during hyperglycemia), and $IR_{@BG70}$ is the infusion rate at BG 70 mg/dL.

During treatment of an individual patient under the algorithm, if glycemic stability is achieved, then the true MR may be assigned. The $MR_{true,stable\ interval}$ is defined to be the mean IR during an interval of stable BG control. Once the $MR_{true,stable\ interval}$ is known, then revised values for G-per-Diem and the $ROA_{max}$ may be defined that improves algorithm performance, when used to estimate population values as defaults upon algorithm initiation for other patients in the future.

In one embodiment, the system may indicate that a default parameter value for G-per-Diem or for $ROA_{max}$ does not fit the patient. Further, the system may inquire about stability of carbohydrate exposure and suggest or implement cautious patient-specific revisions of the values for G-per-Diem and/or $ROA_{max}$.

Correction Rate, Restarting Dose of Insulin, and Simplifications of the General Equation Applied During Hyperglycemia or Euglycemia, Respectively The fundamental equation may be applied to past or future time. The equations may be reduced to simpler equations when ROD or ROA assume the value of zero. The value of zero is assumed by ROD during euglycemia or by ROA during hyperglycemia. The definition of whether the patient is hyperglycemic or euglycemic is determined by $BG_{previous}$ for past time and $BG_{current}$ for future time. In particular, for the exponent to which $MR/IR_{@BG70}$ is raised, during euglycemia when blood glucose is below true target ($BG_{true\ target}$), the exponent is the fractional completeness of ascent of current BG (ascent between 70 mg/dL and true target), which is the same as the fractional reduction of ideal ROA to less than $ROA_{max}$. At $BG = BG_{true\ target}$ or higher, the power to which $MR/IR_{@BG70}$ is raised is 1.

For calculation of $MR_{csne}$, the true target (not upper target) may be used to determine whether the hyperglycemic or euglycemic technique is used for assignment of MR. $MR_{csne}$ is calculable for the next iteration, using $ROD_{previous}$ in the equation applicable during hyperglycemia, whenever $BG_{current} \geq BG_{true\ target}$.

For calculation of CR, the CR is calculated when blood glucose exceeds target. If BG is below target, CR=0. The upper target (not true target) may be used to determine need for CR and target for correction. During piloting of the algorithm, the CR may be calculated for the next iteration only if $BG_{current} \geq BG_{upper\ target}$. The target BG used to calculate $ROD_{ideal,next}$ may be conservatively chosen as $BG_{upper\ target}$.

A fundamental equation of the algorithm for past or future time may have the following equivalent forms:

$$IR = IR_{@BG70} * [e^{[ln(MR/IR_{@BG70})] * FCABG}] * [1 + 24 * (ROD)/(G\text{-per-Diem})]$$

$$IR = IR_{@BG70} * [e^{[ln(MR/IR_{@BG70})] * FRROA}] * [1 + 24 * (ROD)/(G\text{-per-Diem})]$$

$$IR = IR_{@BG70} * [e^{[ln(MR/IR_{@BG70})] * (ROAmax - ROAideal)/(ROA/max)}] *$$
$$[1 + 24 * (ROD)/(G\text{-per-Diem})]$$

In past time, for computation of FCABG, it is necessary to use a calculated past blood glucose at which the observed ROA would have been the $ROA_{ideal}$, specifically:

$$FCABG = \frac{BG_{past} - 70}{BG_{true\ target} - 70} = FRROA = \frac{ROA_{max} - ROA_{ideal}}{ROA_{max}},$$

where $$BG_{past} = BG_{true\ target} - \frac{ROA_{ideal}}{ROA_{max}} * (BG_{true\ target} - 70)$$

During descent of BG from a hyperglycemic value to $BG_{upper\ target}$, the model holds that if insulin is infused at a constant correction rate (CR) in addition to the maintenance rate (MR), then BG will fall at a constant rate ROD. The model holds that ROD is linearly related to the CR and inversely related to the MR. The CR is given as a function of MR and ROD. Equations for CR and IR follow:

CR=MR*24(ROD)/(G-per-Diem)

IR=MR[1+24*(ROD)/(G-per-Diem)]=MR+CR

The correction dose in units of insulin for any given level of hyperglycemia may be represented by the following equation:

"correction dose of insulin"=MR*24*(BG−$BG_{uppertarget}$)/(G-per-Diem)

Under the algorithm, the $ROD_{ideal,next}$ for the first hour of treatment provides for total correction, so that the algorithm delivers this correction dose in the first hour. Generally the correction dose when added to the column maintenance rate fails to achieve correction during the initial hours of treatment, presumably partly because MR is underestimated by the initial column assignment, partly because of lag time for insulin action, and partly because of acute glucose toxicity.

After the first hour, under the algorithm, the $ROD_{ideal,next}$ is conservatively assigned, so that the algorithm does not deliver the entire correction dose after the first iteration.

During ascent of BG from a euglycemic value to $BG_{true\ target}$, the model holds that if insulin is infused at a constant restraining rate IR, such that $IR_{@BG70} \leq IR < MR$, then BG may rise at a constant rate $ROA \leq ROA_{max}$. The model holds that in order to achieve and maintain the $ROA_{ideal}$, the insulin infusion rate IR should be a function of a fractional power of MR, exponentially related to the fractional completeness of ascent of BG. It is recalled that time-to-target= $(BG_{true\ target}-70\ mg/dL)/ROA_{max}$. The IR necessary to restrain the ROA and thus to deliver the $ROA_{ideal}$ is provided by the following simplified equations during euglycemia:

$$IR = IR_{@BG70} * e^{[ln(MR/IR_{@BG70})]*(BG-70)/(BGtrue\ target-70)}$$

$$IR = IR_{@BG70} * e^{[ln(MR/IR@BG70)]*(ROAmax-ROA)/(ROAmax)}$$

where

"restraining dose of insulin" = (time-to-target) $* IR_{restraining\ rate}$

"restraining dose of insulin" =

$(BG_{true\ target} - 70\ mg/dL) / (ROA_{max}) * IR_{restraining\ rate}$

Therefore, the "restraining dose" is provided by the following equation:

"restraining rate" = $(BG_{true\ target} - 70\ mg/dL) / (ROA_{max}) *$ $(IR_{@BG70}) * \langle e^{[ln(MR/IR@BG70)]*[BGcurrent-70)/BGtrue\ target-70)]} \rangle$

Previous Iteration

The previous rate of descent during hyperglycemia ($ROD_{previous}$) or rate of ascent during euglycemia ($ROA_{previous}$) is defined by the precedent measurements of $BG_{previous}$, $BG_{current}$, $time_{previous}$, and $time_{current}$. The insulin infusion rate calculator may use algorithm protocol times rounding to the nearest hour, not computer times for simplification, but computer times of a medical practitioner may be recorded for future analysis.

Cross Step ($MR_{csne}$)

General Equation for Calculation of $MR_{csne}$ from the Previous IR and Rate of Change of BG The $MR_{csne}$ may be calculable at the end of each iteration. Further, the $MR_{csne}$ may provide a more reliable estimate of the true MR when calculated during correction of hyperglycemia than when calculated during ascent of BG on the euglycemic range. The mathematical model for hyperglycemia and euglycemia is described in further detail below. An alternative approach is described below for MR determination during euglycemia.

Calculation of $MR_{csne}$ may require knowledge of previous rate of change of BG and the $IR_{previous}$. Either $ROD_{previous}$ or $ROA_{previous}$ is calculated from actual historical $BG_{previous}$, $BG_{current}$, and $\Delta$ time values. The $ROD_{previous}$ is zero if $BG_{previous} < BG_{true\ target}$. $ROA_{previous}$ is zero and FRROA is 1 if $BG_{previous} \geq BG_{true\ target}$. $ROD_{previous}$ or $ROA_{previous}$ calculated from observations during the previous iteration is used as ROD or $ROA_{ideal}$, respectively, as a precedent in the mathematical model for the calculated $MR_{csne}$, which in turn may be used as a precedent value to calculate $IR_{next}$. The following equations provide for extinguishing one of the variables $ROA_{previous}$ or $ROD_{previous}$ in past time:

$BG_{previous} \geq BG_{truetarget} \rightarrow ROA_{previous}=0$ $BG_{previous} < BG_{truetarget} \rightarrow ROD_{previous}=0$ The equation for insulin infusion rate may be rearranged and applied to past time to calculate $MR_{csne}$. A general equation for $MR_{csne}$ follows:

$MR_{csne}=IR_{@BG70}exp\{ln\ [IR_{previous}/\{(IR_{@BG70})*[1+24*(ROD_{prev,rev})/(G\text{-per-Diem})]\}]*[(ROA_{max}-ROA_{prev,rev})]\}$ This general equation may be reduced to simpler equations by extinguishing either $ROD_{previous}$ or $ROA_{previous}$ depending upon the value of $BG_{previous}$.

Determination of $MR_{csne}$

Determination of $MR_{csne}$ as a Function of $ROD_{previous}$ and $IR_{previous}$ During Correction of Hyperglycemia During hyperglycemia and during descent of BG, at any given $ROD_{previous}$, there exists some MR such that the previous infusion rate of insulin actually used ($IR_{previous}$) would have resulted in the observed rate of descent of BG. Therefore, in order to calculate $MR_{csne}$, the $ROD_{previous}$ is taken to be the ROD that would have resulted during use of $IR_{previous}$, some value for MR and CR (such that MR+CR=$IR_{previous}$), where the fractional contributions of MR and CR to $IR_{previous}$ are determined under the G-per-Diem rule.

During treatment of hyperglycemia, the $ROD_{previous}$ is calculated after each iteration. If $BG_{previous} < BG_{current}$ during hyperglycemia, revision of $ROD_{previous}$ to intermediary $ROD_{previous,revised}$ occurs before ROD is used as an intermediary variable. The unrevised value of $BG_{current}$, even if <70 mg/dL, is used to calculate $ROD_{previous,revised}$ (used when $BG_{previous} \geq BG_{true\ target}$) as provided by the following equations:

$ROD_{previous,revised}=ROD_{previous}$, which is used for $ROD_{previous} \geq 0$; and $ROD_{previous,revised}=-ln([absolute\ value\ of\ ROD_{previous}]+1$, which is used for $ROD_{previous} < 0$.

It is noted that logarithmic adjustment of $ROD_{previous}$ is made for the possibility of rising BG during hyperglycemia, indicating therapeutic failure at the given insulin infusion rate. If the log transform is not performed on $ROD_{previous}$, then during ascent of hyperglycemia-range BG, the equation for $MR_{csne}$ has a vertical asymptote. The asymptote occurs at rates of ascent of BG during hyperglycemia that are physiologically possible, such that $MR_{csne}$ approaches infinity under conditions that actually could occur. Therefore, the log transform is necessary giving $ROD_{previous,revised}$.

The equations for insulin infusion rate may be rearranged to provide the following equation for $MR_{csne}$ for $BG_{previous} \geq BG_{true\ target}$:

$MR_{csne}=IR_{previous}/[1+24*([ROD_{previous,revised}]/[G\text{-per-Diem}])$

Figure 9:
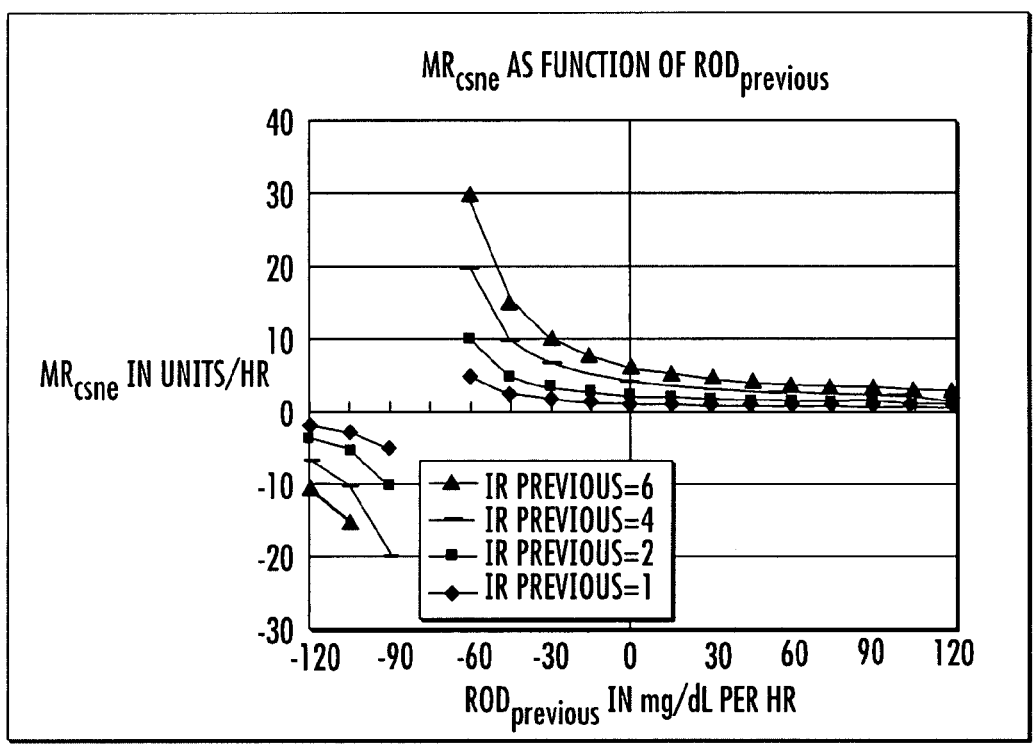
FIG. 9 is a graph showing hyperbola that results from plotting a maintenance rate versus rate of descent with iso-insulin infusion rate curves according to an embodiment of the subject matter disclosed herein.
Figure 10:
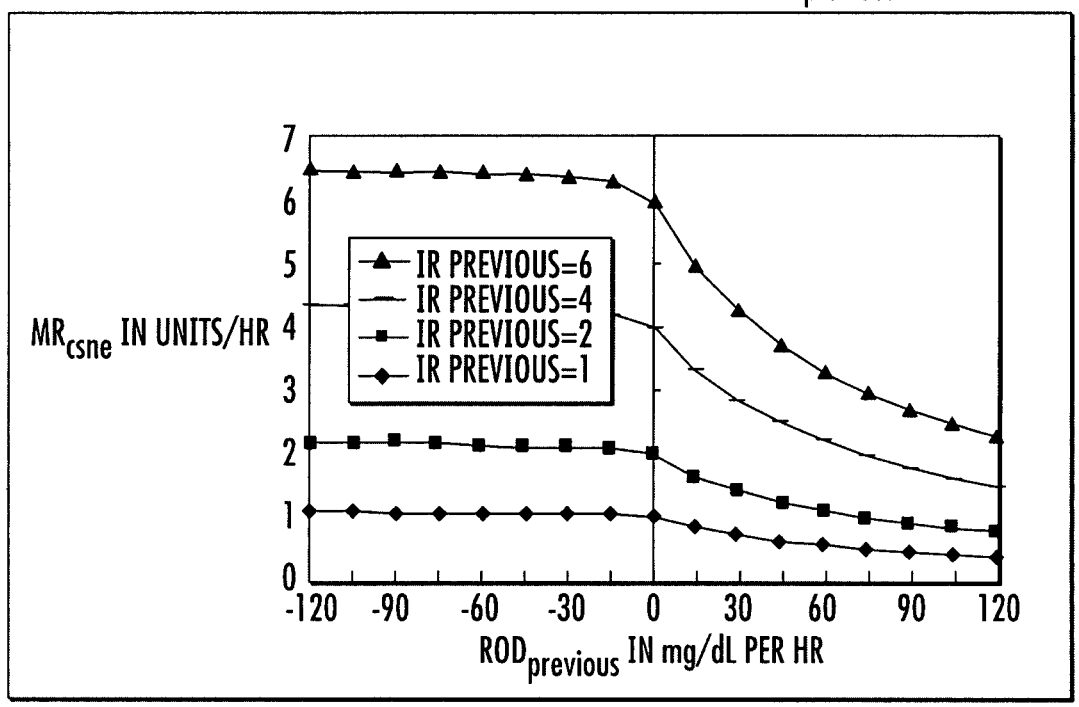
FIG. 10 is a graph showing hyperbola that results from plotting a maintenance rate versus rate of descent with iso-insulin infusion rate curves according to an embodiment of the subject matter disclosed herein.

FIGS. 9 and 10 are graphs showing hyperbola that results from plotting $MR_{csne}$ versus $ROD_{previous}$, with iso-IR curves.

Referring to FIGS. 9 and 10, $MR_{csne}$ is shown as a function of $ROD_{previous}$, calculated without and with a log transform of $ROD_{previous}$ for rising BG. A log transform correction may be made.

Determination of $MR_{csne}$ as a Function of $ROA_{previous}$ and $IR_{previous}$ During Euglycemia When the blood glucose and Δtime values are taken from a previous euglycemic iteration, for BG>70 mg/dL and $ROA_{prev,rev}<ROA_{max}$, it is possible to give an estimation of $MR_{csne}$. If $ROA_{prev,rev}>ROA_{max}$, clearly the value of $ROA_{max}$ has been assigned incorrectly. An alternative method of making arbitrary adjustments of $MR_{csne}$ on the euglycemic BG domain is described in further detail below, without reference to the model that is about to be described.

In this section, it is shown that for any value of $BG_{previous}<BG_{true\ target}$, it is mathematically possible to assign a calculated value for $MR_{csne}$, based on hypothetical measurements of $ROA_{previous}$ and knowledge of $IR_{previous}$, as long as the following conditions are met:

true MR of the patient>$IR_{@BG70}$;
true $ROA_{max}$ of the patient>0 for $IR=IR_{@BG70}$;
$IR_{previous}$ assigned during the previous iteration>$IR_{@BG70}$, if $BG_{previous}$>70 mg/dL;
$IR_{previous}$ assigned during the previous iteration=$IR_{@BG70}$, if $BG_{previous}$=70 mg/dL;
$ROA_{previous}<ROA_{max}$, for any observed value of $ROA_{previous}$ and $BG_{previous}$>70 mg/dL;
$ROA_{previous}=ROA_{max}$, for $BG_{previous}$=70 mg/dL; and
If $BG_{previous}$ was 70 mg/dL, $IR_{previous}$ should have been assigned the value of $IR_{@BG70}$. If the observed value of $ROA_{previous}$ differs from $ROA_{max}$ when $BG_{previous}$ was 70 mg/dL and $IR_{previous}$ was $IR_{@BG70}$, then the value of the parameter $ROA_{max}$ must be reassigned.

The equation for $MR_{csne}$ has a singularity at $ROA_{previous}=ROA_{max}$. An alternative solution at that point exists and is of importance to show the completeness of the model for computation of $MR_{csne}$. In the mathematical model, $MR_{csne}$ as a function of ROA, at BG=70 mg/dL and $ROA=ROA_{max}$, equals $$IR_{@BG70}*e^{(-ROAmax/IR_{@BG70})*[d(IRprevious)/d(ROAprevious)]}.$$

Assume 70 mg/dL<$BG_{previous}<BG_{true\ target}$, and assume ascent of BG is occurring. At any given $BG_{current}$>70 mg/dL, $IR_{previous}>IR_{@BG70}$, and observed $ROA_{previous}<ROA_{max}$, under the model there exists some $MR>IR_{@BG70}$ and some $BG_{past}<BG_{true\ target}$, such that the previous infusion rate of insulin actually used ($IR_{previous}$) would have resulted in the observed rate of ascent of BG and attainment of target $BG_{true\ target}$ at the end of the interval having duration="time-to-target"=($BG_{true\ target}$+70)/$ROA_{max}$. In fact, the $BG_{current}$ if it were determined immediately at the end of the interval "time-to-target" might differ from $BG_{true\ target}$, indicating need for reassignment of the MR as $MR_{csne}$.

In order to calculate $MR_{csne}$, the $ROA_{previous}$ is taken to be the ideal $ROA_{ideal}$ that would have been sought during use of $IR_{previous}$ at some value for $MR>IR_{@BG70}$ and some $BG_{past}<BG_{true\ target}$.

During euglycemia, the following equations may apply for $ROA_{previous,revised}$ when $BG_{previous}>BG_{true\ target}$:

$ROA_{previous,revised}=ROA_{previous}$(this equation used for ROApreviousâ‰¥0; and $ROA_{previous,revised}=-\ln([$absolute value of $ROA_{previous}]+1)$(this equation is used for $ROA_{previous}<0$.

Note that an adjustment was made for the possibility of falling BG during euglycemia, indicating therapeutic failure at the given insulin infusion rate. If the log transform is not performed on $ROA_{previous}$, then at physiologically possible rates of descent of BG during euglycemia, the equation for $MR_{csne}$ potentially predicts an $MR<IR_{@BG70}$, contradicting the assumption of the algorithm that the patient has a requirement for exogenous insulin greater than the negligible infusion delivered at $IR_{@BG70}$. Actually, during descent of euglycemic-range BG, the likelier explanation for falling BG would be that there had been a delay in the dynamic action profile of insulin delivered at a higher infusion rate during an iteration prior to the previous iteration, or a delay in the point-of-care adjustments of infusion rates such that actual time was later than that algorithm time at which commencement of $IR_{previous}$ was intended.

The equations for insulin infusion rate may be rearranged to give the $MR_{csne}$ as shown in the following equation:

$$MR_{csne} = IR_{@BG70} * e^{[ln(IR/IR_{@Bg70})]*(BGtrue\ target-70)/(BGpast-70)}$$

The $BG_{past}$ at which $IR_{previous}$ and the new estimate of $MR_{csne}$ would have worked to achieve $BG_{true\ target}$ within time-to-target, is provided by the following equations:

$BG_{past}=BG_{true\ target}-ROA_{previous,revised}*$(time-to-target)

$BG_{past}=BG_{true\ target}-ROA_{previous,revised}*(BG_{true\ target}-70)/(ROA_{max})$ The following equations result, respectively requiring the inverse of FCABG or the inverse of FRROA in the exponent of the expression for $MR_{csne}$:

$$MR_{csne} = IR_{@BG70} * e^{\frac{[ln(IRprevious/IR@BG70)]*(BGtrue\ target-70)/[BGtrue\ target-ROAprevious,revised*(BGtrue\ target-70)/(ROAmax)-70]}}$$

$$MR_{csne} = IR_{@BG70} * e^{\frac{[ln(IRprevious/IR@BG70)]*(ROAmax)/(ROAmax-ROAprevious,revised)}}$$

Thus, $MR_{csne}$ is a function of two variables, $ROA_{previous,revised}$ and $IR_{previous}$.

Figure 11:
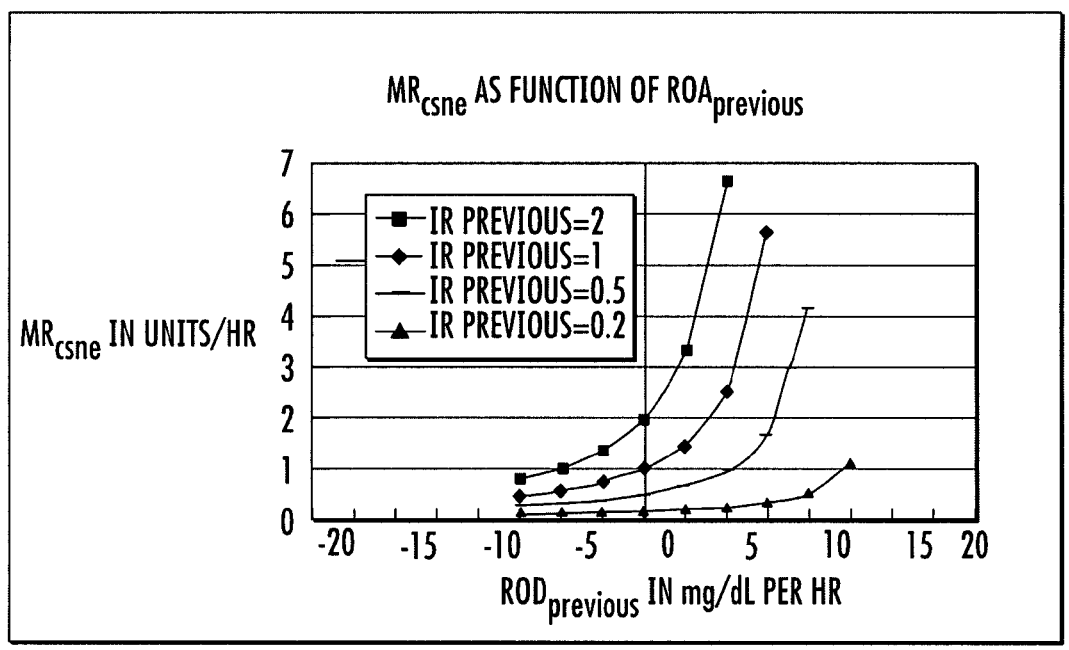
FIG. 11 is a graph showing that results from plotting a maintenance rate versus rate of ascent with iso-insulin infusion rate curves according to an embodiment of the subject matter disclosed herein.
Figure 12:
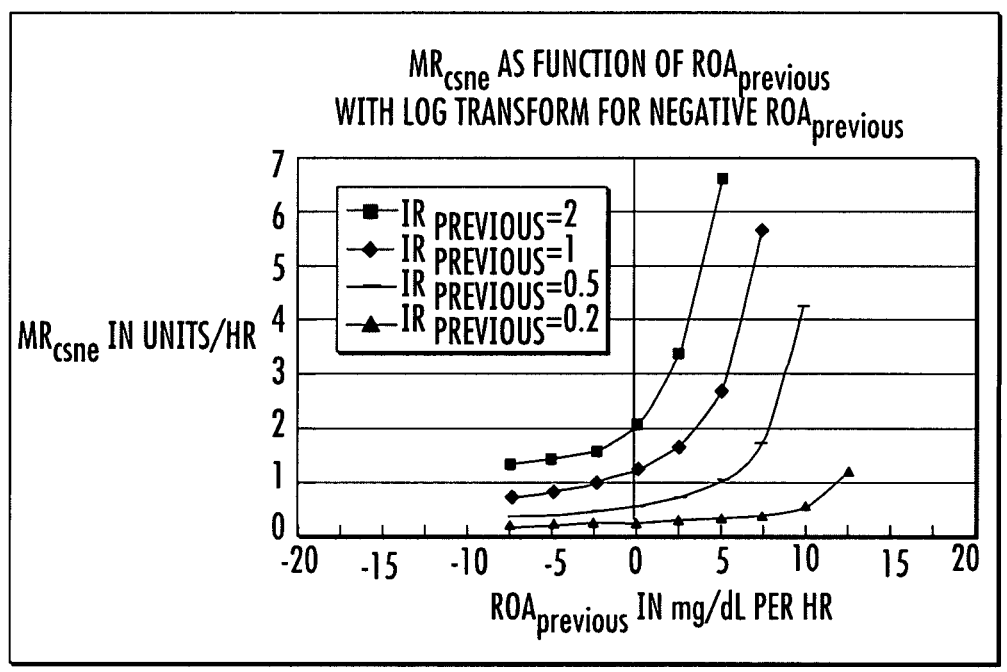
FIG. 12 is a graph that results from plotting a maintenance rate versus rate of ascent with iso-insulin infusion rate curves according to an embodiment of the subject matter disclosed herein.

In FIGS. 11 and 12, graphs are shown that result from plotting $MR_{csne}$ versus $ROA_{previous}$, with iso-IR curves, without and with the log transform applied to $ROA_{previous}$ to deal with negative ROA values. $MR_{csne}$ is plotted against observed $ROA_{previous}$, with assumptions that ROAmax=17.5 mg/dL per hour, that $ROA_{max}$ occurs at BG=70 mg/dL if IR assigned properly at BG=70, and that IR at BG 70/$ROA_{max}$ should have been assigned at $IR_{@BG70}$, which here is 0.1 units per hour. Conversely, assignment of IR to be 0.1 units per hour should be reserved for the condition that BG=70 mg/dL.

Even though it is mathematically possible under the model to calculate the $MR_{csne}$, it may be of little or no practical importance to do so except under defined conditions. One of the principal pitfalls is the possibility that the true value for $ROA_{max}$ for a particular patient will not have been assigned correctly by using a default value for $ROA_{max}$. Any necessary correction to the value of $ROA_{max}$ must be discovered during treatment and entered to the equations before recalculating $MR_{csne}$. Another principal pitfall is that at lower values of $BG_{previous}$, to derive $MR_{csne}$ from $ROA_{previous}$, the necessary increments of time interval and change of BG must become infinitesimally small. Any error in BG measurement (used to determine $ROA_{previous}$) or error in $ROA_{max}$ may be amplified exponentially. Rounding of IR to one or two decimal places introduces error, which carries heaviest impact on calculation of $MR_{csne}$ at very low values of $IR_{previous}$. Recalculation of $MR_{csne}$ during euglycemia thus may lead to gross errors in estimations of $MR_{csne}$, especially below $BG_{lower\ target}$. In actual practice, with the use of continuous sensors, with future possible improvement in exactness and precision of BG measurement, and with continuous reassignment of $IR_{previous}$, even at low levels of $BG_{previous}$, the model could be beneficial.

Nevertheless, the equations of $MR_{csne}$ as a function of rate of change of BG and $IR_{previous}$ have been stated over the entire domain of $BG \geq 70$ mg/dL to demonstrate completeness of the model.

Assignment of $MR_{csne}$ as the Last Value Carried Forward, Revised During Euglycemia Patient treatment courses may be indexed. Within a given indexed patient treatment course, each iteration of the algorithm is given a sequentially assigned "iteration number," used for indexing of measurements and calculations. The initial iteration is given iteration number="1," and each iteration thereafter is numbered sequentially from "1" to "n". For the iteration just completed, the index number is "n". For the iteration about to start, the index number is "n+1". $MR_{csne}$ at the end of iteration "n" is indexed as $MR_{csne}$ (n).

At the end of each iteration, based on risk for hypoglycemia, a decision may be made as to whether $MR_{csne}$ (n) needs revision. There will be arbitrary 20% downward revisions of the value of $MR_{csne}$ (n) in the event of downward BG trend meeting defined criteria. There are other potential adjustments as described in more detail herein. Regardless of whether the value for $MR_{csne}$ (n) needs revision, a new variable is created, and the new variable is given the name $MR_{csne,revised}$ (n).

If $BG_{previous,rev} < BG_{true\ target}$, the last value of $MR_{csne,revised}$, from iteration (n−1) is carried forward to be used as $MR_{csne}$ (n) upon completion of iteration "n". The process of carrying forward is repeated until the next time arrives that $BG_{previous}$ exceeds $BG_{true\ target}$.

When it occurs that $BG_{previous,rev}$ exceeds $BG_{true\ target}$, the $MR_{csne}$ equation for $BG_{previous} \geq BG_{true\ target}$ may be used to recalculate $MR_{csne}$. The following rules may be applied for adjusting and assigning MR for iterations 1 and n+1:

$MR_{csne}$ (1)=$MR_{initial}$, for first iteration, or any iteration following a 2 hour interruption of insulin infusion;

$MR_{csne}$ (n)=value calculated by formula, if $BG_{prev,rev} \geq BG_{true\ target}$;

$MR_{csne}$ (n)=last value carried forward, i.e. $MR_{csne,revised}$ (n−1) is carried forward to become $MR_{csne}$ (n), if $BG_{prev,rev} < BG_{true\ target}$;

Once this has been done, $MR_{csne,hypoglycemia-adjusted}$ (n)=80% of $MR_{csne}$ (n), this adjustment made if $BG_{current,rev} < BG_{lower\ target}$;

$MR_{csne,risk-adjusted}$ (n)=[$MR_{csne,hypoglycemia-adjusted}$ (n)]− (24 hour increment of insulin added to TPN)/(24), this adjustment made if a medical administrator indicates insulin to be increased in the TPN, this change starts when the new TPN bag is hung, this change is made to the $MR_{csne,hypoglycemia-adjusted}$ (If the MR change is a decrement due to insulin in the TPN, the $MR_{csne,TPN-adjusted}$ (n) may be reduced to $IR_{@BG70}$.);

$MR_{csne,risk-adjusted}$ (n)=50% of $MR_{initial}$, this adjustment trumps the previous adjustment if it results in a lower number, and this adjustment is made if the following have been reported or will occur: (1) tube feed interruption, (2) ≥50% rate reduction of dextrose infusion, and interruption of CVVHD;

In the future, using C6R, NR, and BR, adjustments of MR proportionate to actual changes of carbohydrate exposure may be made; and $MR_{csne,revised}$ (n) is defined as the minimum of the $MR_{csne}$ (n) values given above.

The selected value for $MR_{csne,revised}$ (n) is used as a precedent in the equation for $IR_{next}$ when $BG_{previous} < BG_{true\ target}$. In one alternative, automated control may reassign $MR_{csne}$ during euglycemia.

Extinguishing One or Both of the Variables $ROA_{ideal,next}$ and/or $ROD_{ideal,next}$ in Future Time The equation for insulin infusion rate is applied to future time to calculate $IR_{next}$. The $MR_{csne}$, $BG_{current}$ and algorithm parameters are used as precedent values to calculate $ROD_{ideal,next}$ or to calculate $ROA_{ideal,next}$. Since FRROA equals FCABG, the simpler equation for $IR_{next}$ is selected, expressing its exponent in terms of FCABG rather than FRROA. The $ROD_{ideal,next}$ is zero if $BG_{current} < BG_{upper\ target}$. The $ROA_{ideal,next}$ is zero and FRROA is 1 if $BG_{current} \geq BG_{true\ target}$. Extinguishing one or both of the variables $ROA_{ideal,next}$ and/or $ROD_{ideal,next}$ in future time may result in the following:

$$BG_{current} \geq BG_{truetarget} \rightarrow ROA_{ideal} = 0$$

$$BG_{current} < BG_{uppertarget} \rightarrow ROD_{ideal,next} = 0$$

$$BG_{truetarget} \leq BG_{current} < BG_{uppertarget} \rightarrow ROA_{ideal} = 0 \text{ and } ROD_{ideal,next} = 0$$

Relating the Ideal Rate of Change of BG to the Insulin Infusion Rates in Future Time

General Equation for Insulin Infusion Rate for the First and Subsequent Iterations The default MR for the initial iteration is estimated as follows: among adults, normally 2 units/hour for trauma service, burn unit, corticosteroid-treated patients, or severely stressed patients. The default is normally 1 unit/hour for all others. For children, the default is 0.015 units/kg-hour. For the initial iteration, the $ROD_{ideal,next}$ is $(BG_{initial} - BG_{upper\ target})/(time_{next})$, where $time_{next}$ is 1 hour.

A first iteration initial infusion rate of $IR_{initial}$ is provided by the following equations:

$$CR_{initial} = 24*(BG_{initial} - BG_{upper\ target})/(time_{next})/(G\text{-per-Diem})$$

$$IR_{initial} = MR_{initial} + 24*(BG_{initial} - BG_{upper\ target})/(time_{target})/(G\text{-per-Diem})$$

IR for subsequent iterations of the algorithm (IRnext) is provided by the following equations:

$$IR = (IR_{@BG70}) * [e^{[ln(MR/IR@BG70)]*(FCABG)}] *$$
$$[1 + 24*(ROD_{ideal,next})/(G\text{-per-Diem})]$$

$$IR = (IR_{@BG70}) * [e^{[ln(MR/IR@BG70)]*(FRROA)}] *$$
$$[1 + 24*(ROD_{ideal,next})/(G\text{-per-Diem})]$$

$$IR = MR * [1 + 24*(ROD_{ideal,next})/(G\text{-per-Diem})], \text{ for }$$
$$BG \geq BG_{true\ target}$$

$$IR = MR + CR \text{ for } BG \geq BG_{true\ target}$$

$$IR = IR_{previous} * (G\text{-per-Diem} + 24*ROD_{ideal,next})/$$
$$(G\text{-per-Diem} + 24*ROD_{previous})$$

for $BG \geq BG_{true\ target}$ $$IR = (IR_{@BG70}) * [e^{[ln(MR/IR@BG70)]*(BGcurrent-70)/(BGtruetarget-70)}]$$
for $BG < BG_{true\ target}$ $$IR = (IR_{@BG70}) * [e^{[ln(MR/IR@BG70)]*(ROAmax-ROAideal,next)/(ROAmax)}]$$
for $BG < BG_{true\ target}$ $$IR = (IR_{@BG70}) * [(MR/IR_{BG70})^{exp(Fractional\ Completeness\ of\ Ascent\ of\ BG)}]$$
for $BG < BG_{true\ target}$ $$IR = (IR_{@BG70}) * [(MR/IR_{BG70})^{exp(Fractional\ Reduction\ of\ ROAidea,next)}]$$
for $BG < BG_{true\ target}$ The first initial equation above may be reduced to the simpler equations by extinguishing either $ROD_{ideal,next}$ or $ROA_{ideal,next}$ or both, depending upon the value of $BG_{current}$.

Simplified Equation for $IR_{next}$ During Hyperglycemia

During hyperglycemia, for $BG_{current} \geq BG_{true\ target}$, the value for $IR_{next}$ is calculated tentatively as follows. The algorithm may prohibit $IR_{next} >$ maximum IR ($IR_{max}$). $IR_{max}$ is an algorithm parameter having a different value for adults and children, proportionate to $MR_{initial}$. When the equation for $IR_{next,tentative}$ gives a value higher than $IR_{max}$, the value of $IR_{max}$ is substituted, which is by default 36 units per hour for adults and 0.54 units/kg per hour for children.

The following is a simplified equation for $IR_{next}$, when $BG_{current} \geq BG_{true\ target}$:

$$IR_{next,tentative} = MR*[1+24*(ROD_{ideal,next})/(G\text{-per-Diem})]$$

$$IR_{next} = IR_{next,tentative}, \text{ if } IR_{next,tentative} \leq IR_{max}$$

$$IR_{next} = IR_{max}, \text{ if } IR_{next,tentative} > IR_{max}$$

For $BG_{true\ target} \leq BG_{current} < BG_{upper\ target}$, because $ROD_{ideal,next} = 0$, it may be evident that $IR_{next} = MR$.

Simplified Equation for $IR_{next}$ During Euglycemia

During euglycemia, for $BG_{current} < BG_{true\ target}$, the following equations apply:

$BG_{current,rev} = BG_{current}$, if no treatment for hypoglycemia occurred;

$BG_{current,rev} = 70$ mg/dL, if treatment for hypoglycemia occurred (use 70 mg/dL as $BG_{cur,rev}$ even if measured BG after treatment was higher);

$$IR_{next} = (IR_{@BG70}) * e^{[ln(MR/IR@BG70)]*[(ROAmax-ROAideal,next)/(ROAmax)]}$$

$$IR_{next} = (IR_{@BG70}) * e^{[ln(MR/IR@BG70)]*[(BGcur,rev-70)/(BGtruetarget-70)]}$$

During euglycemia, the equations for $IR_{next}$ give an asymmetric approximately sigmoidal curve between BG 70 mg/dL and $BG_{upper\ target}$. For the future, the equations giving $IR_{next}$ may be replaced by a logistic equation.

Iterations Straddling Euglycemia and Hyperglycemia

In the course of a single iteration, the $BG_{previous}$ and $BG_{current}$ values may straddle the euglycemic and hyperglycemic ranges. For a patient or population, if $ROA_{max}$ is found to differ from the default value, and if time-to-target for that given $ROA_{max}$ is substantially shorter than 2 hours, overshoot of BG may occur before a 2 hour test time has arrived. The $ROA_{max}$ does not directly appear in the expression for $IR_{next}$. The $ROA_{max}$ may determine time-to-target and the restraining dose of insulin.

To prevent overshoot of BG, the time-to-target may be predicted using $ROA_{max}$ and to require a BG test at that predicted time, so that after passage of time the IR then may be reassigned to equal MR, once BG is confirmed to be at $BG_{true\ target}$. Irregularly timed BG testing may place a burden upon medical administrators.

To prevent overshoot of BG while still maintaining a regular schedule for testing, a more aggressive strategy may be to partition the time between BG tests ($\Delta$Time) into two parts:

(1) the expected duration of time before reaching target; and (2) the expected duration of time after reaching target, requiring BG thereafter to be maintained at target until the next test time.

Time-weighting may be used to assign $IR_{next}$. Safety of this more aggressive approach may be tested.

Time-weighted aggressive modification of IRnext for prevention of overshoot during ascent of BG is provided by the following equation:

$$IR_{next} = \{(\text{time-to-target})*(IR_{@BG70})*$$
$$e^{[ln(MR/IR@BG70)]*[(BGcur,rev-70)/(BGtruetarget-70)]} +$$
$$[(\Delta time) - (\text{time-to-target})]*MR\},$$

where this {quantity} divided by ($\Delta$time), and where time-to-target is determined by $ROA_{max}$. A similar strategy may be used if overshoot is predicted to occur during descent of BG. Even though overshoot does occur during descent, it may be difficult to predict because the equations during correction of hyperglycemia are designed to achieve partial correction and therefore predict undershooting.

Prevention of Hyperglycemia

A data entry screen of a system in accordance with the subject matter described herein may query the medical practitioner on whether reduction of carbohydrate exposure or other predictors of hypoglycemia will occur. For positive responses from the practitioner, anticipatory down-titration rules for the value of MRcsne, in a manner similar to column down-titration rules, may be applied for reassigning $MR_{csne}$ as $MR_{csne,risk-adjusted}$.

If a patient is receiving intravenous insulin infusion and is taking discrete meals, anticipatory subcutaneous injections of rapid acting insulin analog may be provided prandially to stabilize the insulin infusion rate and to prevent overshooting hyperglycemia that may result from reactive IR adjustments.

Response to Hypoglycemia

The data entry screen may query the practitioner as to whether hypoglycemia has occurred subsequent to the previous data entry. A positive response may prompt a recommendation for treatment of hypoglycemia and retesting of BG (if untreated), and may prompt a query on whether a change of carbohydrate exposure has occurred, and whether the change of carbohydrate is expected to be sustained.

For $BG_{current}$ below 70 mg/dL, correction with intravenous dextrose may be provided to achieve BG≥70 mg/dL. The BG is repeated, retreatment with 50% dextrose is offered if necessary, and finally BG>70 mg/dL is achieved. Regardless of the value, $BG_{current,revised}$ is given a value of 70 mg/dL. The $MR_{csne}$ is hypoglycemia-adjusted to 80% of its previous value.

Next BG Test Time

Goals important to the medical practitioners include the reduction of BG testing frequency from every one hour to every two hours and avoidance of irregularly timed results. Under the system described herein, the following rules may be applied:
(1) The indications for BG monitoring every 1 hour include:
  algorithm initiation
  increase or decrease of continuous carbohydrate exposure, planned to be a sustained revision of delivery rate>4 hours in duration
(2) Monitoring every 2 hours may be recommended when:
  no plan exists for sustained increase or decrease of carbohydrate exposure>4 hours in duration
  MR is stable as defined below:
  (a) greater than or equal to 4 hours have elapsed since algorithm initiation
  (b) concordance score for MR=3 for the past 3 consecutive determinations of MR (n)
    if 0.67<(MR(n−1)/MR(n))<1.5, score=1
    if not, score=0
    concordance score=sum of past three determinations
  (c) within the past 4 hours, no $BG<BG_{lower\ target}$ has occurred.
Once the time interval has been adjusted to every 2 hours, the default for $time_{next}=2$ hours. However, if $IR_{next}$ is revised by the practitioner to a value higher than recommended by the algorithm, the fact of the practitioner-designated upward revision of $IR_{next}$ may result in assignment of test $time_{next}$ to be 1 hour after test $time_{current}$. Other criteria for reversion to hourly monitoring include
  increase or decrease of continuous carbohydrate exposure, planned to be a sustained revision of delivery rate>4 hours in duration
  destabilization of glycemic control.
  1) $BG_{current,revised}<BG_{lower\ target}$
  2) $BG_{current,revised}>BG_{upper\ target}\times 8$ hours (likely to be useful during advancement of feed tubes)
  3) $BG_{current,revised}>BG_{critical\ high}\times 2$ hours, and BG not falling at $ROD_{ideal,next}$ or faster
  4) MR reassignment to 50% of $MR_{initial}$ for any reason
overshoot of BG above $BG_{upper\ target}$ predicted at given value of $BG_{current}<BG_{true\ target}$ according to revision of $ROA_{max}$ for population or patient (parameter for severity of overshoot that would justify revision and predictive computation are described in more detail below in the section "Discovery of the Value of $ROA_{max}$")

Special Populations

Revised and higher target ranges are identified for children and for renal failure patients. Strategies for renal failure include changing the default $BG_{true\ target}$ to a higher number. When the HR is activated, it may introduce a correction for renal failure. Another possible strategy is to reduce the ideal rate of descent at BG 180 mg/dL from 30 mg/dL per hour to a lesser value, in the presence of renal failure.

In order to meet the American Diabetes Association (ADA) standard for treatment of diabetic ketoacidosis and HHS, the algorithm default for each of these emergency conditions identifies a high value for $BG_{true\ target}$. These alternative defaults were chosen so that the calculations of the algorithm would yield the same $BG_{upper\ target}$ that is identified in the ADA standards. When the $BG_{true\ target}$ is fixed in this manner to preserve the ADA $BG_{upper\ target}$, the recalculated $BG_{lower\ target}$ comes out lower than the threshold given in the ADA standard. Therefore, an intervention is added that will preserve the $BG_{lower\ target}$ of the ADA standard. The algorithm may call for negligible insulin infusion at BG values below the ADA lower target. The default value for $ROA_{max}$ is stated to be 70 mg/dL per hr and $ROD_{ideal,next,max}$ is stated to be 150 mg/dL per hr. During initiation of therapy for hyperglycemic emergency, for one to several hours during which initial rehydration occurs, a rehydration-related decline of blood glucose occurs as well as insulin-induced decline of blood glucose. An initially estimated insulin infusion maintenance rate $MR_{initial}$ may be carried forward unchanged to become the next insulin infusion maintenance rate MR during the first several treatment hours during which rehydration is occurring. After rehydration the algorithm re-estimates the insulin infusion maintenance rate based on the glycemic response of the patient at a previous insulin infusion rate. The value of $BG_{critical\ high}$ and the ideal ROD at $BG_{critical\ high}$, are redefined to be consonant with the ADA standards set forth in the publication "Hyperglycemic Crises in Adult Patients with Diabetes: A Consensus Statement from the American Diabetes Association", by Kitabchi et al., *Diabetes Care*, 29 (12): 2739-48 (2006), the disclosure of which is incorporated by reference herein in its entirety.

Revision of User-Defined Parameter Values

Revision of the Value of $BG_{true\ target}$

A user-defined upward adjustment of $BG_{true\ target}$ may be made. For recurrence of hypoglycemia within the same treatment course, or for any BG<50 mg/dL, not explained by transitory interruption of carbohydrate exposure, a specific recommendation may be made to the medical practitioner to accept a 20% upward revision of the parameter $BG_{true\ target}$.

Revision of $ROD_{@BGcritical\ high}$

Another type of user-defined modification may be to reduce the $ROD_{ideal,next}$ by down-scaling the ROD$_{@BGcritical\ high}$. This may be best done for application to specific cases at high risk for hypoglycemia or with proven history of hypoglycemia.

Stable Intervals

For the purpose of calculating mean values on stable intervals, the termination of a stable interval may be identifiable only by retrospective review. Stable intervals of at least 8 hours in duration may be identified that were preceded by hyperglycemia, initiated by normoglycemia, and terminated in one of three ways: (1) by hyperglycemia meeting criteria for destabilization; (2) by hypoglycemia; and (3) by interruption of the sequence of evaluable timepoints by meeting of exclusion criteria for specific timepoints. Time-weighted mean $IR_{next}$ on stable intervals may be calculated.

Timepoints defining the start and end of a stable interval may be determined by application of the following rules used to define the stable interval, and additional exclusion criteria may be applied to the interval as a whole:

1) Defining the Start of a Stable Interval

The start time of a stable interval may be marked by the test $time_{current}$ identified with the first $BG_{current}$ in stable interval. Timepoints, identified as below, may be considered as candidates for the start to the interval if they meet the following inclusion and exclusion criteria:

a) Inclusion criteria qualifying test $time_{current}$ to mark the start of a stable interval include:

$BG_{lower\ target} \leq BG_{current} \leq BG_{upper\ target}$ at test $time_{current}$ two consecutive hyperglycemic BG measurements $\geq BG_{upper\ target}$ immediately prior to test $time_{current}$, with times not exceeding 2 hours between BG measurements;

b) The earlier hyperglycemic BG, if it followed a recorded change of carbohydrate exposure or change of insulin in TPN, may be required to have occurred at least 2 hours subsequent to the recorded change. Exclusion criteria, disqualifying test $time_{current}$ to mark the start of a stable interval may be:

interruption of $BG_{current}$ or $IR_{next}$ data for >2 hours immediately preceding test $time_{current}$ interruption of insulin infusion within 2 hours immediately preceding test $time_{current}$ Defining the End of a Stable Interval BG measurements occurring after the start of the stable interval may be evaluated in sequential order. The end of a stable interval may be marked by the test $time_{current}$ identified with the final BG in the stable interval. Timepoints may be considered to end a stable interval if any of the following conditions are met:

Each BG subsequent to the first BG of the candidate interval may be classified as being within the range $70 \leq BG < 140$ mg/dL or not (140 for adult patients). When inclusion of $BG_{next}$ would reduce the percent of BGs lying within range to <80%, the candidate interval may be terminated with inclusion of the immediately preceding BG, which will be identified as the final BG in the stable interval.

When a BG has value $\geq BG_{critical\ high}$, or when two consecutive values for BG have values $\geq 140$ mg/dL, the candidate interval may be terminated with inclusion of the immediately preceding BG, which may be identified as the final BG in the stable interval.

If BG<70 mg/dL is observed, a candidate interval may be terminated at the timepoint identified with the last eligible BG before the appearance of BG<70 mg/dL Additionally, timepoints terminate a stable interval, and $BG_{current}$ and $IR_{previous}$ may be considered the last data of their kind from the stable interval under condition of the following:

The final iteration for the treatment course ended with this timepoint

Interruption of $BG_{current}$ or $IR_{next}$ for >2 hours began at this timepoint (i.e. $time_{next}$>2 hours)

Interruption of insulin infusion for >2 hours began at this timepoint

Documented change of carbohydrate exposure occurred simultaneous with $BG_{current}$(n) or between $BG_{current}$(n) and $BG_{current}$(n+1).

Documented change of insulin in TPN occurred simultaneous with $BG_{current}$(n) or between $BG_{current}$(n) and $BG_{current}$(n+1)

Exclusion Criteria for Stable Intervals

Exclusion criteria for stable intervals include the following:

Upward or downward trend excluded the interval (if, for the entire interval, each BG was higher than the predecessor, or each BG lower than the predecessor, the interval may be discounted as a stable interval and the timepoints excluded)

An interval may be excluded if timepoints within stable interval did not span 8 hours after the initial $BG_{upper\ target}$, including the ending timepoint of the interval An interval may be excluded if fewer than 3 BG measurements were available for averaging Calculations on Stable Intervals The numbers may be counted of stable intervals, patients having any stable interval, and patients with diabetes having any stable interval. Peaks of BG within stable intervals may be identified by searching each time segment between appearance of BG<110 mg/dL for the highest $BG \geq 110$ mg/dL that occurred on that time segment. A completed minor oscillation may be defined by occurrence of two peaks of $BG \geq 110$ mg/dL within a given stable interval. Each stable interval may be evaluated as to how it was terminated (high BG, low BG or exclusion criteria for a timepoint), and by the numbers of peaks of BG, completed oscillations between peaks, and hours spanned by completed oscillations.

Blood glucose data may be assessed without and with log-transform. The mean BG on stable intervals may be calculated. The BG at test $time_{current}$ marking the start of the candidate interval may be excluded from averaging of BGs within the candidate interval. The BG at the final timepoint of the stable interval may be included in the averaging and may be the last BG to be included.

Unstable Intervals

Unstable intervals of 8 hours duration may be identified that were preceded by hyperglycemia and initiated by normoglycemia according to the criteria for stable intervals, but were designated as unstable and terminated as candidate stable intervals in one of two ways before 8 hours had elapsed, by hyperglycemia meeting criteria for destabilization, or by hypoglycemia.

Stochastic Approach to Determination of Parameter Values

The algorithm is designed to work even if medical practitioner entries about carbohydrate exposure are not made. The algorithm therefore may be blind to upward adjustments of carbohydrate exposure that may occur in the timeframe of treatment. A stochastic approach to determination of parameter values is justified only on stable intervals. Within the collection of measurements used for averaging, the putative determinant(s) for the parameter value may be similar (specifically, data might be classified according to whether energy provided as nutritional support meets daily requirements or does not).

Discovery of the Value of $MR_{true}$

The time-weight mean $IR_{next}$ may be calculated during each stable interval. The $IR_{next}$ assigned at the test $time_{current}$ that defines the start of the candidate interval, may be included in averaging of IRs within the candidate interval and may be the first $IR_{next}$ to be included in the averaging. If the data sheet or electronic record indicates that the insulin infusion was running but practitioner entry of the infusion rate was missing the hourly value for $IR_{next}$ may be assigned as zero, and the value of zero may be included in the averaging. The $IR_{next}$ assigned at the test time prior to the final BG within the stable interval may be the last $IR_{next}$ to be included in the averaging. The $IR_{next}$ assigned at the test $time_{current}$ of the final BG, i.e. at the final timepoint of the stable interval, may be excluded from the averaging.

The time-weighted mean IR on the stable interval, $IR_{mean,stable\ interval}$ may be taken as an estimate of true MR ($MR_{true}$) at the time of a stable interval, computable by retrospective review. Computation of MRtrue may be provided by use of the following equation:

$$MR_{true} = IR_{mean,stableinterval}$$

$MR_{csne}$ may converge to a stable value. Further, $MR_{true,stable\ interval}$ may be close to $MR_{csne}$ before convergence.

The ability to define a value for $MR_{true}$ for individuals may not occur in real time because stable intervals are not identifiable in real time. Nevertheless, it may be necessary to have a value of $MR_{true}$ for individuals determined retrospectively in order to define individual values for the other algorithm parameters C-per-Diem and $ROA_{max}$ and arrive at population averages.

Discovery of the Value of G-Per-Diem for Populations

Accurate knowledge of MR is useful for revision of the value of G-per-Diem. $ROD_{previous}$ and $IR_{previous}$ may be used together with $MR_{true}$ to make an estimated reassignment of the value of G-per-Diem, to be called G-per-$Diem_{revised}$. Population averages may be defined so that the parameter is assigned at the outset of treatment according to the likely needs of the patient. If the applicable population average is used, for any given patient the equations for $IR_{next}$ during euglycemia may exhibit better performance with respect to assignment of $MR_{csne}$ and less tendency to overcorrection or undercorrection of hyperglycemia.

Records may be examined retrospectively. Stable intervals during the treatment course of any patient may be segregated according to whether or not maintenance energy needs were provided. The values of G-per-Diem, calculated upon entrance to a stable interval and during any stable interval, may be averaged for stable intervals. Population averages with and without provision of maintenance energy needs may be defined as the average of the patient averages.

At timepoints defining entry to a stable interval for which $BG_{previous} \geq BG_{upper\ target}$ and $BG_{lower\ target} \leq BG_{current} < BG_{upper\ target}$, the last $BG \geq BG_{upper\ target}$ prior to the interval may be used as $BG_{previous}$, and the first $BG < BG_{upper\ target}$ may be used as $BG_{current}$. At timepoints occurring during a stable interval, in order to recalculate G-per-Diem it is required that $BG_{previous}$ exceed $BG_{upper\ target}$ and also that the BG before $BG_{previous}$ exceeds $BG_{upper\ target}$.

The time between $BG_{previous}$ and $BG_{current}$ (1 or 2 hours) may be used as $time_{previous}$ in order to calculate $ROD_{previous}$. G-per-Diem then may be given by the following equation for computation of G-per-Diem at individual timepoints for retrospective discovery of population average:

$$\text{G-per-Diem}_{revised} = (ROD_{previous})*(MR_{true}*24\ hr)/(IR_{previous} - MR_{true})$$

Population averages may be calculated according to diagnosis category and nutritional energy provided, called G-per-$Diem_{population}$.

Discovery of the Value of G-Per-Diem for Individuals in Real Time

Error in the technique of point-of-care monitoring of blood glucose may introduce error into parameter recalculation, such that individually recalculated values for G-per-Diem may not likely be useful. Nevertheless, individuals may have values that differ from the population average. The computation for individual timepoints within an apparent stable interval may be conducted as follows, with intent of maintaining a running average, for computation of G-per-Diem at individual timepoints for real-time discovery of patient average:

$$\text{G-per-Diem} = (ROD_{previous})*(MR_{csne,revised}*24\ hr)/(IR_{previous} - MR_{csne,revised})$$

With the use of $MR_{csne,revised}$ instead of $MR_{true}$ for real-time computation during stable intervals, the running average of G-per-Diem may be provided. The running average may be used in case an individual, while treated using the default value or population average for G-per-Diem, manifests inappropriate response to correction during hyperglycemia (insufficient correction or overcorrection of hyperglycemia).

Figure 13:
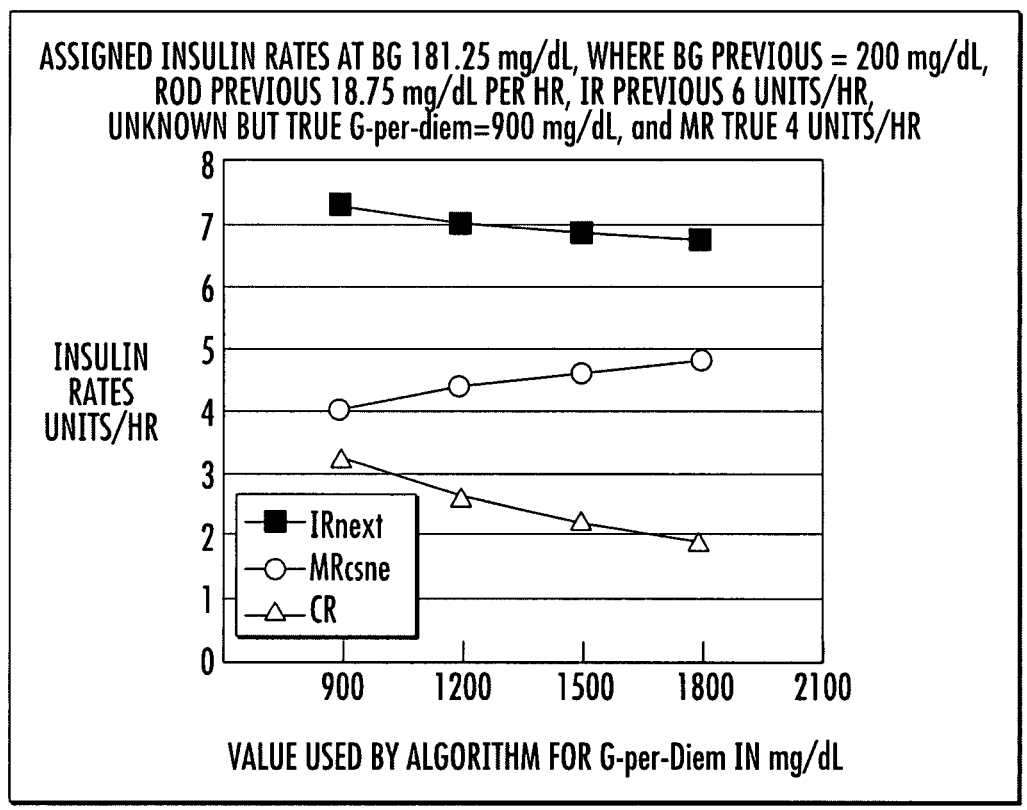
FIG. 13 is a graph showing insulin rates versus values for G-per-Diem according to an embodiment of the subject matter disclosed herein.

During correction of hyperglycemia, when lower and higher values of G-per-Diem are compared, the use of a higher value for G-per-Diem gives a slightly higher $MR_{csne}$ but slightly lower CR and $IR_{next}$, as shown in FIG. 13, which is a graph of insulin rates versus value used by the algorithm for G-per-Diem. In FIG. 13, the insulin rates that would be assigned by the algorithm at $BG_{current}=181.25$ mg/dL are shown for various values used by the algorithm for G-per-Diem, for a patient whose demonstrated $ROD_{previous}$ was 18.75 mg/dL per hour, at $IR_{previous}=6$ units per hour, and whose unknown G-per-Diem actually is 900 mg/dL and $MR_{true}$ is 4 units per hour. During descent of BG, as $IR_{next}$ approaches $MR_{true}$, the $IR_{next}$ and $MR_{csne}$ converge to the value of $MR_{true}$. Within an order of magnitude, it may be expected that the choice of value of G-per-Diem to have only a small impact, such that patient safety would not be affected.

Discovery of the Value of $ROA_{Max}$ for Populations

Accurate knowledge of MR is necessary for revision of the value of $ROA_{max}$. $ROA_{previous}$ and $IR_{previous}$ may be used together with $MR_{true}$ to make an estimated reassignment of the value of $ROA_{max}$, to be called $ROA_{max,revised}$. Population averages may be defined so that the parameter may be assigned at the outset of treatment according to the likely needs of the patient. If the applicable population average is used, for any given patient the equations for $IR_{next}$ or the determination of $testtime_{next}$ may exhibit better performance with respect to euglycemic ascent by reducing overshoot to values above $BG_{true\ target}$.

The algorithm may require that the BG has been $<BG_{true\ target}$ for at least one iteration prior to the previous iteration (a timeframe assumed sufficient for washout of higher insulin infusion rates). For $IR_{previous}<MR_{csne}$, the equation for $ROA_{max,revised}$ is derived as follows:

$$IR_{previous} = IR_{@BG70} * e^{[(ROAmax-ROAprevious)/ROAmax]*ln(MRcsne/IR@BG70)}$$

$$ROA_{max} * [\ln(MR_{csne}/IR_{@BG70}) - \ln(IR_{previous}/IR_{@BG70})] = ROA_{previous} * \ln(MR_{csne}/IR_{@BG70})$$

Computation of $ROA_{max}$ at individual timepoints for retrospective discovery of population average is provided by the following equations:

$ROA_{max,revised} = ROA_{previous,revised} * [\ln(MR_{true}/IR_{@BG70})/\ln(MR_{true}/IR_{previous})]$, for 70 mg/dL$<BG_{previous}<BG_{truetarget}$ $ROA_{max,revised} = ROA_{previous,revised}$, for BGprevious=70 mg/dL and $IR_{previous}=IR_{@BG70}$ $ROA_{max}$ may be assigned with the confidence only under the defining conditions for this parameter, in the situation that $BG_{previous}$ was 70 mg/dL, such that $IR_{previous}$ was $IR_{@BG70}$. The equation above is used on the assumption that the exponential model correctly relates insulin infusion rates to the ROA. The $ROA_{max}$ may be calculated only if $BG_{previous,rev}<BG_{true\ target}$. The revision of the value of $ROA_{max}$ may only work if $IR_{previous}$ and MR have been correctly assigned, such that the MR used in the equation approximates the true MR. $MR_{true}$ may be used in the equation. Further, $ROA_{max}$ may be determined by using the average IR on a stable interval as an estimate of MR in the equation above.

The following may be necessary and exclusionary conditions for calculations leading to revision of $ROA_{max}$:
(necessary) n=2 or greater
(necessary) $BG_{previous,rev}$ (n)$<BG_{true\ target}$
(necessary) $BG_{previous,rev}$ (n−1)$<BG_{true\ target}$
(necessary) if $BG_{cur,rev}>BG_{previous,rev}$, then $IR_{previous}<MR_{true}$.
(necessary) if $BG_{cur,rev}<BG_{previous,rev}$, this may only be calculated only if $IR_{previous}>MR_{true}$
(exclusionary) if BG is unchanged, then $IR_{previous}=MR_{true}$, and this equation cannot be used During ascent of blood glucose, a higher value for $ROA_{max}$ results in a reduction of time-to-target. The revised value of $ROA_{max}$ may be used in at least two ways: (1) to change the next test time; or (2) to replace the calculated $IR_{next}$ with an IR calculated to deliver the restraining dose of insulin over 2 hours. For considerations of safety, the algorithm may assign an earlier test time (1 hour instead of 2 hours, if gross overshoot is predicted). By preventing overshoot by 2 hours due to rising BG, hyperglycemic oscillations and correction therapy leading to subsequent hypoglycemia may be avoided.

The following equation is an overshoot equation for $BG_{future}$:

$BG_{future}=BG_{current}+\Delta time*ROA_{max}*[(BG_{true\ target}-BG_{current})/(BG_{true\ target}-70\ mg/dL)]$ Rearranging the equation for prediction of BG, any value of $ROA_{max}$ may be determined at what threshold $BG_{current}$ there would occur overshoot values exceeding $BG_{upper\ target}$, before 2 hours had elapsed. When excessive overshoot by 2 hours is predicted at $BG_{current}$ for a given $ROA_{max}$, BG testing may occur at 1 hour.

Discovery of the Value of $ROA_{max}$ for Individuals

Sufficient timepoints may be available to permit accurate reassignment of $ROA_{max}$ during real-time treatment of an individual patient. Error in the technique of point-of-care monitoring of blood glucose may introduce error into parameter recalculation, such that individually recalculated values for $ROA_{max}$ are not reliable. Most data points are likely to be excluded. The following factors may be considered in excluding a data point:

There are combinations of values for $IR_{previous}$ and MR that do not yield reasonable results;

If BG is rising, $IR_{previous}$ must be <MR and must be assigned by algorithm

If BG is falling, then $IR_{previous}$ by definition must exceed MR. In other words, if the algorithm was used to assign $IR_{previous}$ and if the BG was falling on the euglycemic range, then the MR used to assign $IR_{previous}$ was no the true MR If the BG is falling on the euglycemic range, another possibility is that the MR was correct but that the algorithm was not used to assign $IR_{previous}$ If BG is unchanged, it is assumed that $IR_{previous}$ was MR, and $ROA_{max}$ may not be calculated by the equation above Holdover effect from the insulin infusion rate of a previous iteration may still be acting Nevertheless, it may become obvious that individuals may have values that differ from the population average. The last $MR_{csne}$ carried forward from iteration "n−1" may be used in the equation, after convergence of $MR_{csne}$ over several iterations has been assured. The computation for individual timepoints within an apparent stable interval may be conducted as follows, with intent of maintaining a running average for $ROA_{max}$. The following equation may be used for computation of $ROA_{max}$ at individual timepoints for real-time discovery of patient average:

$ROA_{max}=ROA_{previous}*(BG_{truetarget}-70)/(BG_{truetarget}-BG_{previous})$

The running average may be used in case an individual, while treated using the default value or population average for $ROA_{max}$, manifests inappropriate rebound hyperglycemia during ascent of blood glucose from the lower end of the target range.

Although $ROA_{max}$ may be calculated simply from BG data, the calculation may not be valid unless $MR_{true}$ was used to assign IR at the time of measurement of $BG_{previous}$. The following equation may be used for computation of $ROA_{max}$ at individual timepoints for real-time discovery of patient average:

$ROA_{max}=ROA_{previous,revised}*[\ln(MR_{csne,revised}/IR_{@BG70})/\ln(MR_{csne,revised}/IR_{previous})]$ Insulin-to-Carbohydrate Ratio The nutritional rate (NR) and basal rate (BR) may be components of MR. The NR is the rate of insulin infusion needed to cover carbohydrate exposure, and BR is the rate necessary to present unchecked gluconeogenesis and ketogenesis. The rate of exposure to carbohydrate in gm/hour is the carbohydrate infusion rate (C6R). If BR is known, then, once an insulin-to-carbohydrate ratio is established, it is possible to re-estimate NR and MR after changes to C6R occur. A common assumption for patients eating normal meals is that maintenance rate=basal+nutritional insulin; basal=40-50% of TDDI; and nutritional=50-60% of TDDI.

In the presence of medical stress during hospitalization, the absolute amount of each component, basal and nutritional insulin, is altered. Calculations on a "per kilo" basis for maintenance insulin, and calculations on a "per gm carbohydrate" basis for nutritional insulin, are likely to be misleading. Compared to these "per kilo body weight" and "per gram carbohydrate" rules for basal and nutritional insulin, the actual requirements discovered during intravenous insulin infusion are more likely to lead to correct assumptions about the immediate insulin needs of the patient.

Anticipatory adjustments to MR may be made to cover changes of carbohydrate exposure using knowledge of (1) MRtrue; (2) carbohydrate exposure at the time $MR_{true}$; and (3) rules dividing daily insulin maintenance requirement into basal and nutritional components, for patients receiving enteral and parenteral nutrition.

Assuming that daily energy needs are not grossly overprovided or underprovided, the insulin-to-carbohydrate ratio at a given level of medical stress is fairly consistent, where $$(insulin/carb)ratio = NR_{previous}/CR_{previous} = NR_{incremental}/C6R_{incremental} = NR_{next}/C6R_{next}$$

$$NR_{incremental} = [C6R_{incremental} * (NR_{previous}/C6R_{previous})]$$

$$NR_{next} = [C6R_{next} * (NR_{previous}/C6R_{previous})]$$

Therefore, when a change of carbohydrate exposure is foreseen, depending on anticipated duration, it may be viewed as a temporary increment to the MR, where $$MR_{next,temporary} = BR + NR_{previous} + NR_{incremental}$$

or it may be viewed as a need for a new $NR_{energy\ maint}$ and new MR, where $$MR_{next,"true"} = BR + NR_{next}$$

At the outset, the algorithm may be blind to upward adjustments of carbohydrate. There may be a risk in anticipating increased insulin requirement before it has happened. The concept of ratio of insulin-to-carbohydrate may be used for down-scaling MR in anticipation of possible hypoglycemia. The interface of a system in accordance with the subject matter described herein may query a practitioner about carbohydrate exposure.

Rate of Delivery of the Hypoglycemic Action of Insulin (HR)

In one embodiment, the rate of delivery of the hypoglycemic action of insulin (HR) may replace IR in adaptations of some of the equations. The algorithm may utilize the rate of delivery of the hypoglycemic action of insulin $HR_{previous}$ rather than $IR_{next}$ in order to achieve the intended rate of change of BG. This may be important for renal failure patients.

A simple assumption for future time is that $IR_{next} = HR_{next}$. For hyperglycemia levels of $BG_{previous}$ in past time, $HR_{previous}$ may be a function of: (1) GFR; (2) $time_{previous}$; (3) the IR value from the previous hour; and (4) the IR value from one or more hours prior to the previous hour. An assumption is that $HR_{previous} = IR_{previous}$.

As an example of a simplifying assumption to account for lag of the hypoglycemic effect of insulin for patients having normal renal function, a 15-minute time shift might be presupposed, so that the conversion between HR and IR may be defined by the following equations:

If $time_{previous}=1$ hour and GFR≥30 cc/min, then $$HR_{previous} = (0.25)*(IR_{minus\ 2\ hr}) + (0.75)*(IR_{minus\ 1\ hr})$$

If $time_{previous}=2$ hours and GFR≥30 cc/min, then $$HR_{previous} = (0.125)*(IR_{minus\ 3\ hr}) + (0.5)*(IR_{minus\ 2\ hr}) + (0.375)*(IR_{minus\ 1\ hr})$$

If $time_{next}=1$ hour and GFR≥30 cc/min, then $$HR_{next} = (0.25)*(IR_{previous}) + (0.75)*(IR_{next})$$

If $time_{next}=2$ hours and GFR≥30 cc/min, then $$HR_{next} = (0.125)*(IR_{previous}) + (0.875)*(IR_{next})$$

For the first iteration, it may be assumed that HR=(0.75)*IR.

Depending upon precedent values, even the simplified mathematical treatment of pharmacodynamics presented above may lead to unreasonable mathematical results using the equations of this algorithm (negative infusion rates may be calculated, or the equations may lead to division by zero). If a negative insulin rate is computed for the next iteration by using $HR_{next}$, the algorithm output will be construed as a signal to administer bolus carbohydrate according to an insulin-to-carbohydrate ratio.

An oversimplification may be to suppose that the problem of lag time of the hypoglycemic action of insulin can be addressed by simple introduction of a 15 minute offset of action during intravenous insulin infusion. Insulin effect is not delivered as an instantaneous pulse following insulin bolus injection, nor is the effect of a square wave of infusion delivered as a square wave of pharmacodynamic action, offset in time into the future. The timecourse of effect may be complex, and the parameters determining the lag time of insulin action may differ depending upon duration of hyperglycemia, exposure to exogenous insulin in the immediate timeframe, adequacy of tissue perfusion and transcapillary exchange, and the determinants of hyperglycemia (peripheral clearance of carbohydrate versus unchecked hepatic glucogenesis).

Figure 14:
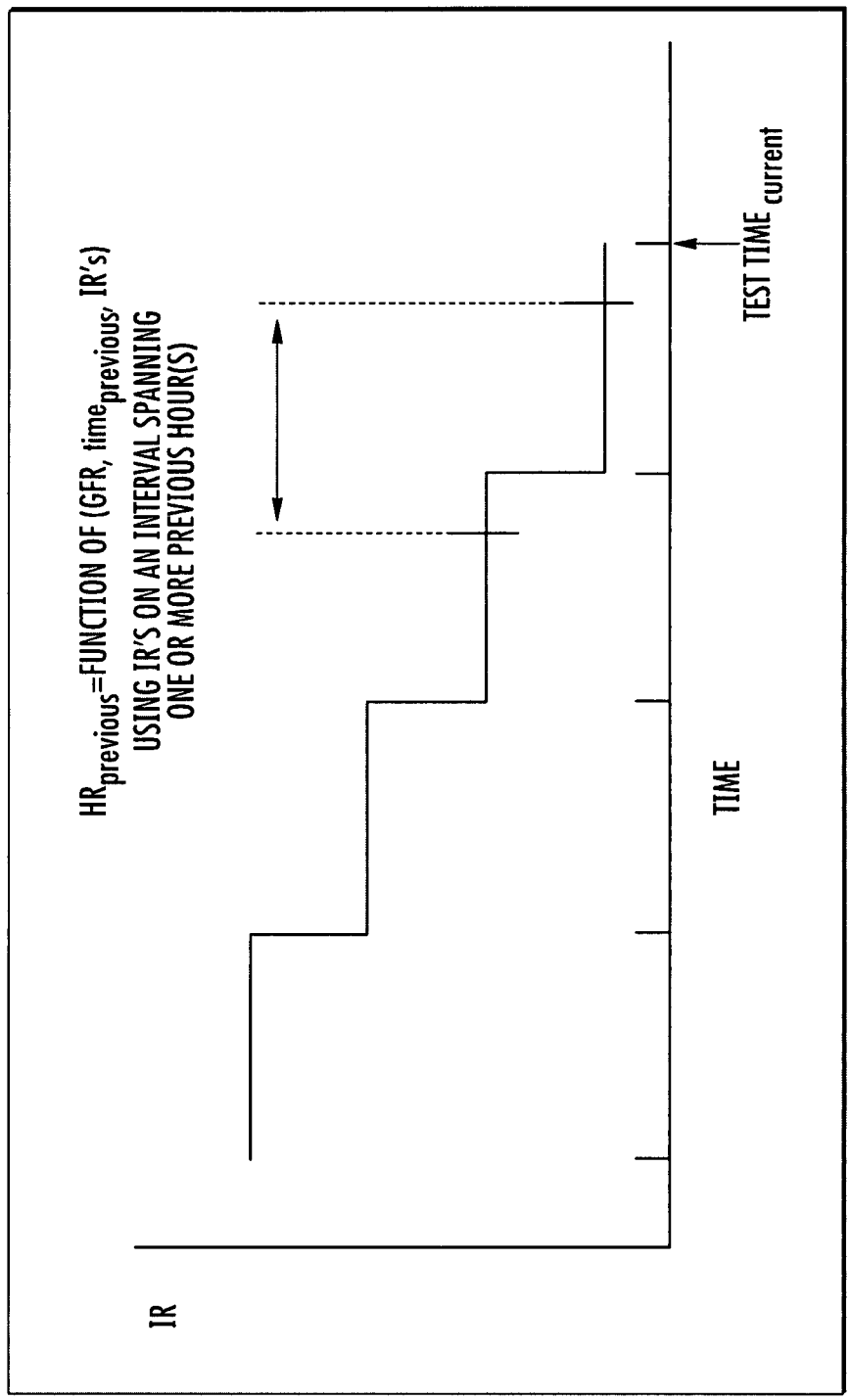
FIG. 14 is a graph showing an insulin infusion rate versus time as the domain for computation of rate of delivery of the hypoglycemic action of insulin (HR) according to an embodiment of the subject matter disclosed herein.

Clinical experience teaches that in the presence of renal failure, the pharmacodynamic effect may be prolonged even though pharmacokinetics of insulin may be not greatly affected. In one model, the instantaneous HR may be a complex function of time and of instantaneous IR during a previous time span of duration and onset determined by the GFR, as shown in the graph shown in FIG. 14. In FIG. 14, $HR_{previous}$ may be function of GFR, $time_{previous}$, and the IR(s) on time intervals prior to test $time_{current}$, such that the hypoglycemic effect noted between the previous and current test time is determined by the insulin infusion rates during a time interval starting shortly before the previous test time and ending shortly before the current test time.

Conditions for Implementation of $MR_{csne}$ on the Euglycemic Range

Under the algorithm design for piloting according to one embodiment, on the euglycemic range $MR_{csne}$ may not be calculated but may be carried forward or modified after it has been assigned a value during correction of hyperglycemic.

The upper part of the range where $BG_{lower\ target} \leq BG_{current} \leq BG_{true\ target}$, recalculation of $MR_{csne}$ may give reasonable results by the equations of the algorithm for $MR_{csne}$ on the euglycemic range. Calculations of $MR_{csne}$ generated during euglycemia from timepoints in actual treatment courses may be utilized. Since accurate determination of not only $ROA_{previous}$ but also $IR_{previous}$ is necessary for calculation of $MR_{csne}$ during euglycemia, it may be unlikely that the calculated values for $MR_{csne}$ are reasonable unless $HR_{previous}$ replaces the use of $IR_{previous}$ in the equations for $MR_{csne}$.

Opening Screen, Returning Screens, Screen Output, Chart Output, Output for Program File A system in accordance with the subject matter described herein may include a user interface suitable for presenting information from a medical practitioner and for presenting information to the medical practitioner. For the first iteration of a treatment course of a patient, the medical practitioner may enter the $BG_{current}$. For subsequent iterations, $IR_{previous}$ and $BG_{current}$ may be needed for a practitioner to enter.

In one embodiment, burn unit medical practitioners may enter the following: (1) maintenance fluids containing dextrose with infusion rate; (2) dextrose content of TPN with infusion rate; (3) insulin content; and (4) tube feeds. Carbohydrate infusion rates may be calculated in grams. Riders containing dextrose may not be entered.

A return screen may display information about the four types of infusions with infusion rate, present "test time next," and query the practitioner whether any of the information has changed or about to change before "test time next". An MR may be revised downward if there has been or will be reduction of dextrose in the maintenance fluids, reduction of dextrose in the TPN, increase of insulin in the TPN, or reduction of tube feeds between "test time previous" and "test time next". Information about carbohydrate exposure and TPN insulin additive may be used to reduce insulin rates. Subsequent revisions of the algorithm may permit additional material to be displayed and additional entries to be made on an opening and returning screen.

Programming Language and Hardware

According to one embodiment, the systems and methods described herein may be implemented by any suitable computing device and coded in the Java programming language. For example, the systems and methods described herein may be implemented on a desktop computer, a laptop computer, or portable electronic device. Further, the results of patient treatment using the systems and methods described herein may be downloaded to an institutional program file and to institutional patient records. Alternatively, a portable electronic device may be dedicated to the patient for the duration of treatment, then results downloaded to institutional patient records, and a memory of the device cleared of data.

Toward a Family of Asymmetric Sigmoidal Curves for $IR_{next}$ $IR_{next}$ may be represented as a family of equations, differing according to $MR_{true}$, each showing $IR_{next}$ as a function of $BG_{current}$ (see e.g., FIG. 6). The range of $IR_{next}$ is bounded at the lower end by $IR_{@BG70}$. For a given MR, between $BG_{true\ target}$ and $BG_{upper\ target}$, $IR_{next}$ is constant. The range of $IR_{next}$ is restricted by an upper bound for the value of $ROD_{ideal,next}$ and the $IR_{next}$ itself is bounded by a maximum value. The equation for $IR_{next}$ is composed of a linear component for $BG_{current} \geq BGupper$ target and an exponential component for $BG_{current} < BG_{true\ target}$. In one embodiment, fragmentation of the equations relating IR as a function of BG into an exponential and a linear component permits analysis of the algorithm parameters according to the algorithm models.

In another embodiment, fragmentation may not be needed for calculation of $IR_{next}$. The equations may be represented as a family of asymmetric sigmoidal curves (logistic functions), as functions of $BG_{current}$, differing according to $MR_{true}$. An approximation of the asymmetric sigmoidal curve may be constructed by creating: (1) exponential ascent of $IR_{next}$ for $BG_{current} < BG_{upper\ target}$; (2) a relatively flat curve between $BG_{true\ target}$ and $BG_{upper\ target}$ where $IR_{next} = MR$; and (3) exponential damping of ascent of $IR_{next}$ to asymptote, for values of $BG_{current} > BG_{true\ target}$. The value of $IR_{next}$ on the flat segment, or in other words the value of MR, may identify each member of the family of curves according to MR (See e.g., FIGS. 15 and 16).

Figure 15:
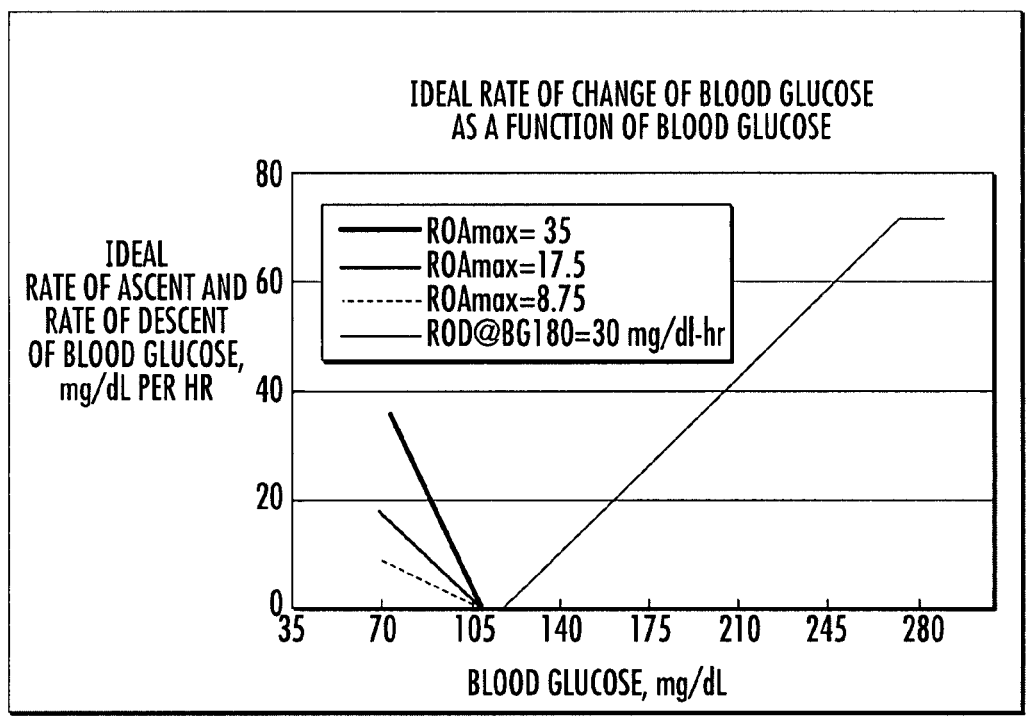
FIG. 15 is a graph of a linear model for ideal rate of change of blood glucose concentration for describing rates of ascent and descent according to an embodiment of the subject matter disclosed herein.
Figure 16:
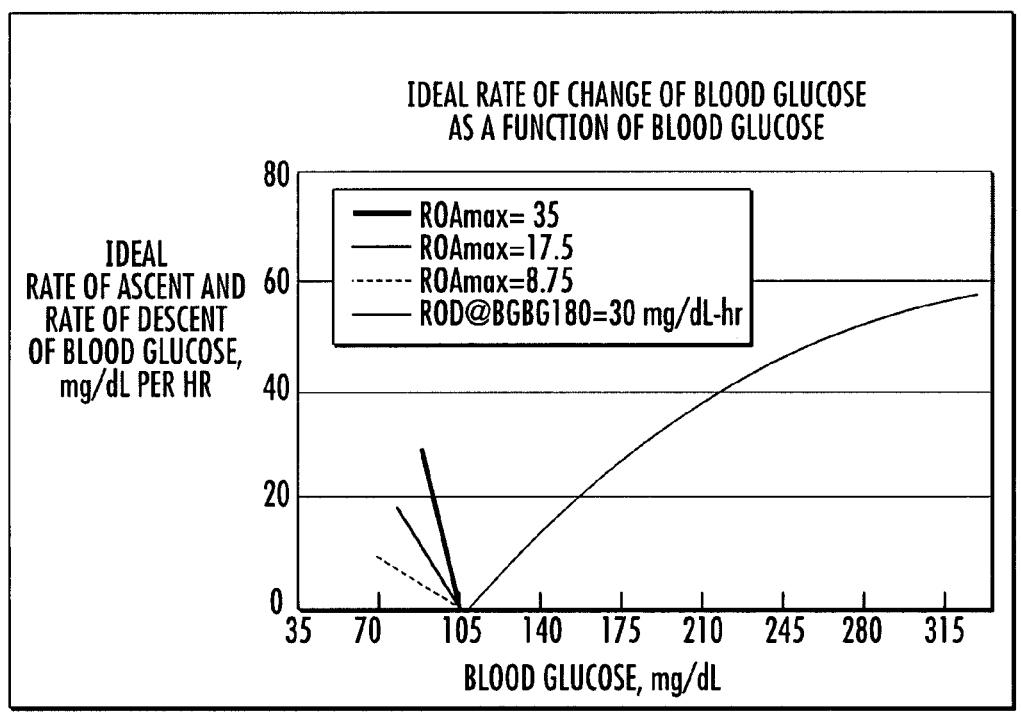
FIG. 16 is a graph of a linear model for ideal rate of ascent of blood glucose concentration for describing rate of ascent and a negative exponential asymptotic model for describing ideal rate of descent according to an embodiment of the subject matter disclosed herein.

FIGS. 15 and 16 are graphs relating an ideal rate of ascent and rate of descent of blood glucose to a target BG. In FIG. 15, a linear model for ideal rate of change of BG is used to describe $ROA_{ideal,next}$ and $ROD_{ideal,next}$, with $ROD_{ideal,max} = 70$ mg/dL per hour. On the narrow interval $BG_{true\ target} \leq BG_{current} < BG_{upper\ target}$ (105-110 mg/dL), $ROA_{ideal,next}$ and $ROD_{ideal,next}$ equal zero. In FIG. 16, a revised model for ideal rate of change of BG as a function of $BG_{current}$ holds that $ROD_{ideal,next}$ is an inverse negative exponential function of $BG_{current}$, increasing to asymptote $ROD_{ideal,max}$ (70 mg/dL per hour).

Figure 17:
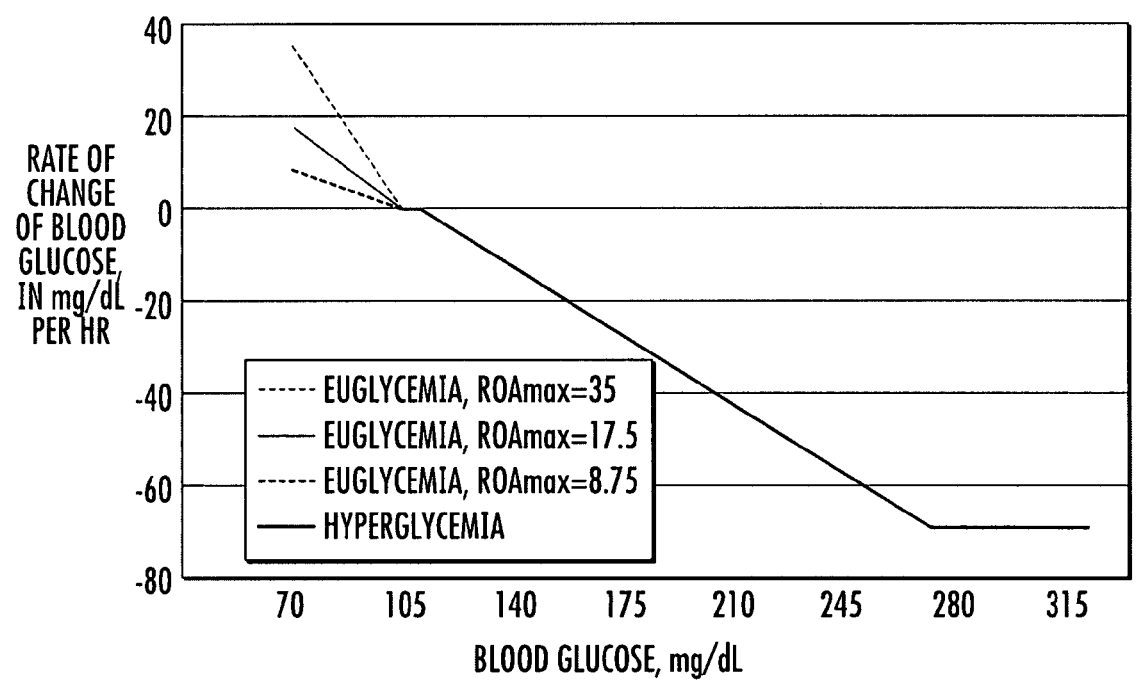
FIG. 17 is a graph of an ideal rate of change of blood glucose as a function of blood glucose according to an embodiment of the subject matter disclosed herein.
Figure 18A:
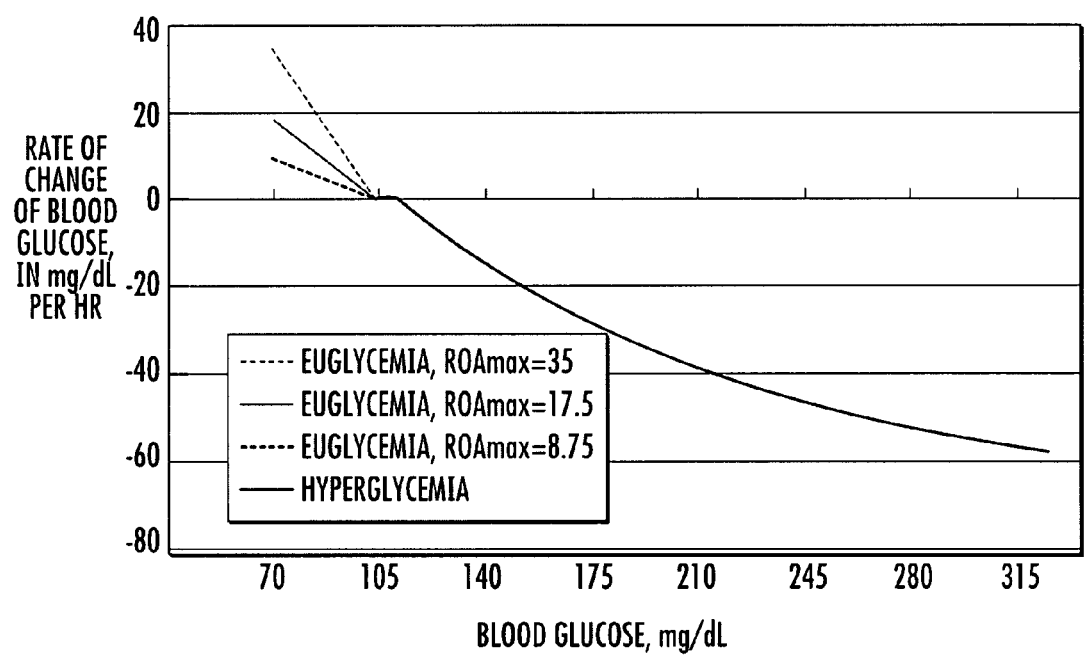
FIG. 18A is a graph of an ideal rate of change of blood glucose as a function of blood glucose according to an embodiment of the subject matter disclosed herein.

FIGS. 17 and 18A are graphs of the ideal rate of change of blood glucose as a function of blood glucose where a medical practitioner defines $ROD_{max} = 70$ mg/dL, $ROD_{@BG}$ 180 mg/dL=30 mg/dL per hour, $BG_{upper\ target} = 110$ mg/dL, and $BG_{true\ target} = 105$ mg/dL. In FIG. 17, to describe $ROA_{ideal,next}$ and $ROD_{ideal,next}$, a linear model for ideal rate of change of BG as a function of $BG_{current}$ is used, with $ROD_{ideal,max} = 70$ mg/dL per hour. On the narrow interval $BG_{true\ target} \leq BG_{current} < BG_{upper\ target}$ (here, 105-110 mg/dL), $ROA_{ideal,next}$ and $ROD_{ideal,next}$ equal zero.

Figure 18B:
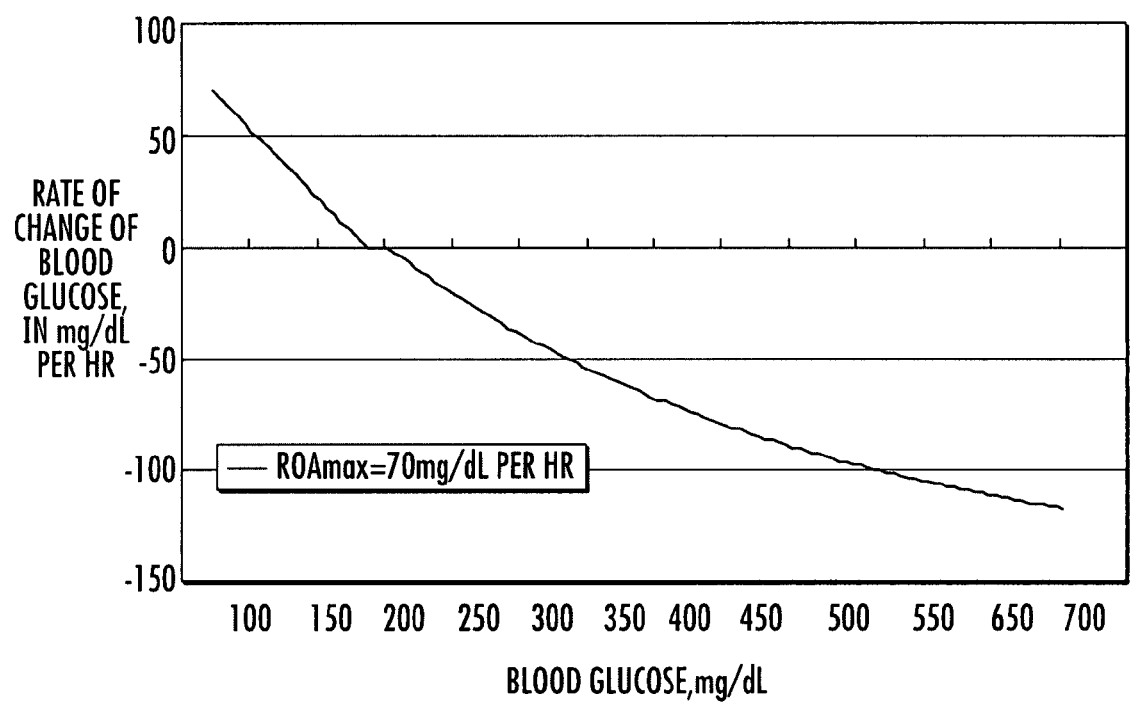
FIG. 18B is a graph of an ideal rate of change of blood glucose for diabetic ketoacidosis as a function of blood glucose according to an embodiment of the subject matter disclosed herein.

In FIGS. 18A and 18B, a model for ideal rate of change of BG as a function of $BG_{current}$ holds that the $ROD_{ideal,next}$ is an inverse negative exponential function for $BG_{current}$, increasing to asymptote $ROD_{ideal,max}$, here 70 mg/dL per hour, or rate of change of blood glucose −70 mg/dL per hour in FIG. 18a and −150 mg/dL per hr in FIG. 18B. The interval on which $ROD_{ideal,next} = ROA_{ideal,next} =$ zero mg/dL per hour may be broader in ketoacidosis and nonketotic hyperosmolar hyperglycemic state, and may be set at a higher range of BG concentrations.

In FIG. 18B, the following defaults are set for diabetic ketoacidosis: $ROD_{max} = 150$ mg/dL per hour, $ROD_{@BGcritical\ high} = 75$ mg/dL per hour, $BG_{critical\ high} = 427.5$ mg/dL, $BG_{upper\ target} = 200$ mg/dL, and $BG_{true\ target} = 183.75$ mg/dL. The computation of $ROD_{ideal,next}$ refers to insulin-mediated decline of BG, with recognition that rehydration-related decline of BG occurs at the same time as insulin-mediated decline. In the undesired situation of attainment of BG=70 mg/dL, $ROA_{max}$ is assumed to 70 mg/dL per hour.

Figure 19:
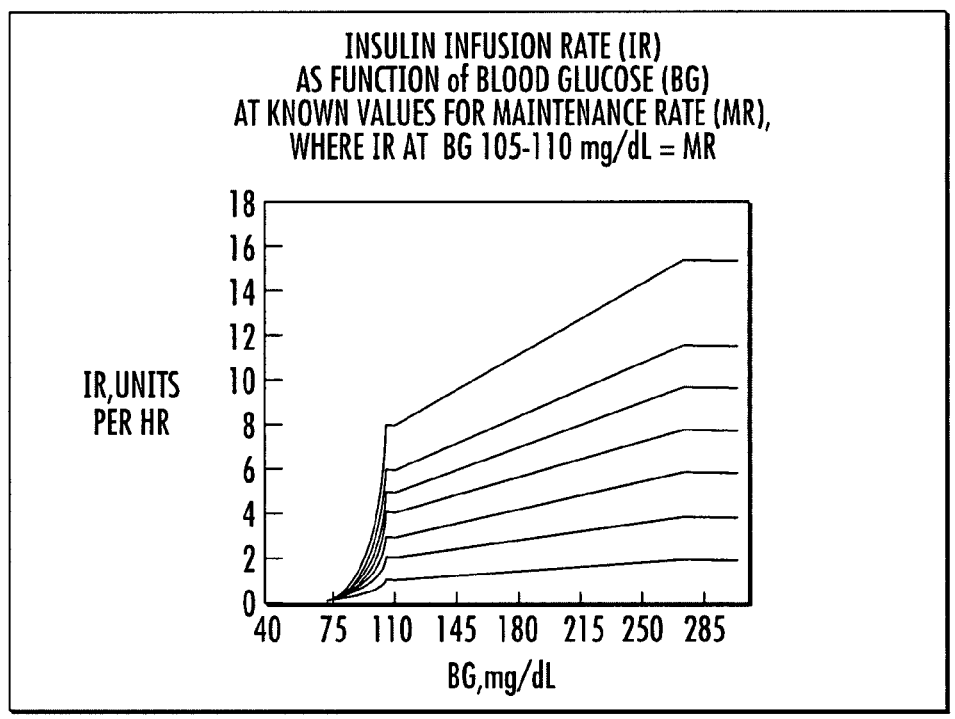
FIG. 19 is a graph of a family of iso-maintenance rate curves showing an insulin infusion rate as a function of blood glucose at known values for maintenance rate according to an embodiment of the subject matter disclosed herein.
Figure 20A:
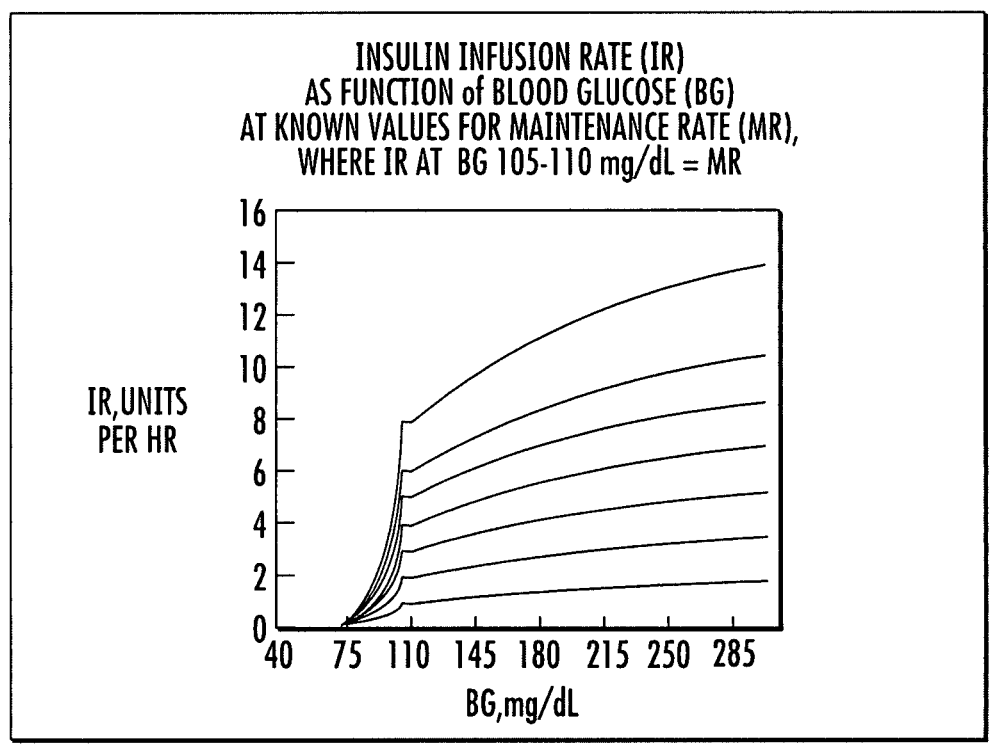
FIG. 20A is a graph of a family of iso-MR curves showing insulin infusion rates as functions of blood glucose at known values for maintenance rate according to an embodiment of the subject matter disclosed herein.
Figure 20B:
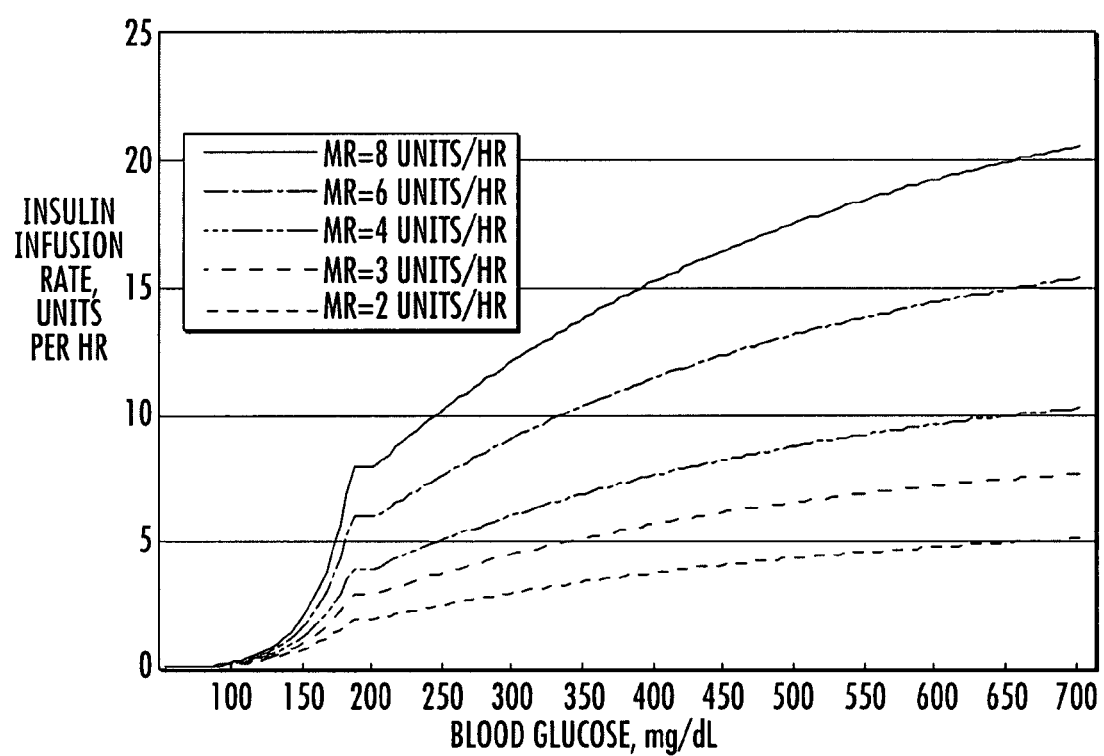
FIG. 20B is a graph of a family of iso-MR curves showing insulin infusion rates for diabetic ketoacidosis as functions of blood glucose at known values for maintenance rate according to an embodiment of the subject matter disclosed herein.

FIGS. 19, 20A, and 20B are graphs of an insulin infusion rate as a function of BG at known values for MR, where IR at BG 105-110 mg/dL=MR in FIGS. 19 and 20A, and IR at BG 184-200 mg/dL=MR in FIG. 20B. FIGS. 19, 20A, and 20B each show a family of functions consisting of multiple iso-MR curves. On the basis of the value of MR determined by the algorithm a patient is assigned or reassigned to an iso-MR function at the beginning of every iteration of the algorithm.

The $IR_{next}$ in FIGS. 19, 20A and 20B is assigned according to $ROA_{ideal,next}$ or $ROD_{ideal,next}$, either of which is dependent upon $BG_{current}$, and $IR_{next}$ is graphed as a function of $BG_{current}$. Below $BG_{true\ target}$, on the euglycemic range, $IR_{next}$ is exponentially related to $(ROA_{max}-ROA_{ideal,next})/ROA_{max}$, which is defined as the FRROA, and which equals the FCABG. On the hyperglycemic range $IR_{next}$ is linearly related to $ROD_{ideal,next}$ and in FIGS. 20A and 20B is a negative exponential function of $BG_{current}$. The ascent of $IR_{next}$ during euglycemia, and the ascent during hyperglycemia, are separated by a narrow interval between $BG_{true\ target}$ and $BG_{upper\ target}$ (105-110 mg/dL in FIG. 20A and 184-200 mg/dL in FIG. 20B) on which $IR_{next}=MR_{true}$. In FIGS. 20A and 20B, a family of asymmetric, approximately sigmoidal curves is created, differing according to MR. The interval on which $IR_{next}=MR$ may be broader in ketoacidosis and non-ketotic hyperosmolar hyperglycemic state, and may be set at a higher range of BG concentrations.

In FIG. 20B, a family of functions for insulin infusion rate as a function of BG for diabetic ketoacidosis is provided. A default initial assumption may be that MR=3 units per hour. When fluids containing 5% dextrose are added, the algorithm can recalculate MR to a higher value.

Assymetric Sigmoidal Curve

To address the problem of hyperglycemia, at given MR, a linear relation between IR and BG may be applied. $IR_{next}$ is assigned in direct proportion to the distance of $BG_{current}$ from target. The maximum value of $IR_{next}$ may be restricted in order to prevent excessively rapid decline of BG. Alternatively it may be stated that the maximum value of $IR_{next}$ is restricted in recognition of saturation effects of insulin action that occur at high infusion rates, such that ROD in excess of $ROD_{ideal,next,max}$ is unlikely to occur at any higher infusion rate. Particularly, the value of $IR_{next}$ may be restricted by limiting the value of $ROD_{ideal,next}$ to $ROD_{ideal,next,max}$ and calculating $IR_{next}$ in linear relation to $ROD_{ideal,next}$.

The segmented linear algorithm in accordance with the subject matter described herein creates two discontinuities in the derivative of $ROD_{ideal,next}$ on the hyperglycemic range, shown at $BG_{upper\ target}$ and at the value of $BG_{current}$ at which $ROD_{ideal,next,max}$ occurs (see e.g., FIG. 5). To eliminate discontinuity at the BG at which $ROD_{ideal,next,max}$ occurs, the algorithm may be configured such that the value of $ROD_{ideal,next}$ approaches an asymptote.

By expressing $IR_{next}$ as a rising exponential function of BG on the euglycemic range when $BG_{current}$ is below true target BG, and as a rising asymptotic negative exponential function of BG on the hyperglycemic range when $BG_{current}$ is above upper target BG, the algorithm is configured as an approximately sigmoidal or doubly sigmoidal curve. It is possible to achieve an approximation of a sigmoidal relationship by one of (1) expressing $ROD_{ideal,next}$ as a negative exponential function of BG and expressing $IR_{next}$ as a linear function of $ROD_{ideal,next}$, or (2) expressing $ROD_{ideal,next}$ as a linear function of BG and expressing $IR_{next}$ as a negative exponential function of $ROD_{ideal,next}$.

It is possible to create the families of curves such that each curve is a continuous strictly increasing logistic function giving $IR_{next}$ as a function of $BG_{current}$.

Future BG as a Function of Time, and Time to Half-Correction, During Continuous BG Monitoring and Continuous Revision of Ideal Next Rate of Change of BG With continuous revision of $ROD_{ideal,next}$ such as might occur with continuous monitoring of BG, the time to half-correction of current BG from the starting BG ($BG_{starting}$) may be calculated. The example given below utilizes the linear model for determination of $ROD_{ideal,next}$.

Future BG Prediction and Time-to-Half Correction During Hyperglycemia with Continuous BG Monitoring and Continuous Revision of $ROD_{ideal,next}$ During descent of BG, the following equation applies:

$$d(BG)/(dt) = -ROD = -(ROD_{@BGcritical\ high})*(BG-BG_{upper\ target})/(BG_{critical\ high}-BG_{upper\ target})$$

By separating variables and integrating, the following equations result:

$$d(BG)/(BG-BG_{upper\ target}) = -(ROD_{@BGcritical\ high})*(dt)/(BG_{critical\ high}-BG_{upper\ target})$$

$$\ln(BG)/(BG-BG_{upper\ target}) = -(ROD_{@BGcritical\ high})*(t)/(BG_{critical\ high}-BG_{upper\ target})+C$$

To define the constant C by looking at one point having given conditions, the time may be zero at the starting time when $BG=BG_{starting}$.

boundary conditions→[($BG_{starting}$)in mg/dL,(zero)in hr]

$$\ln(BG-BG_{upper\ target}) = C$$

Figure 21:
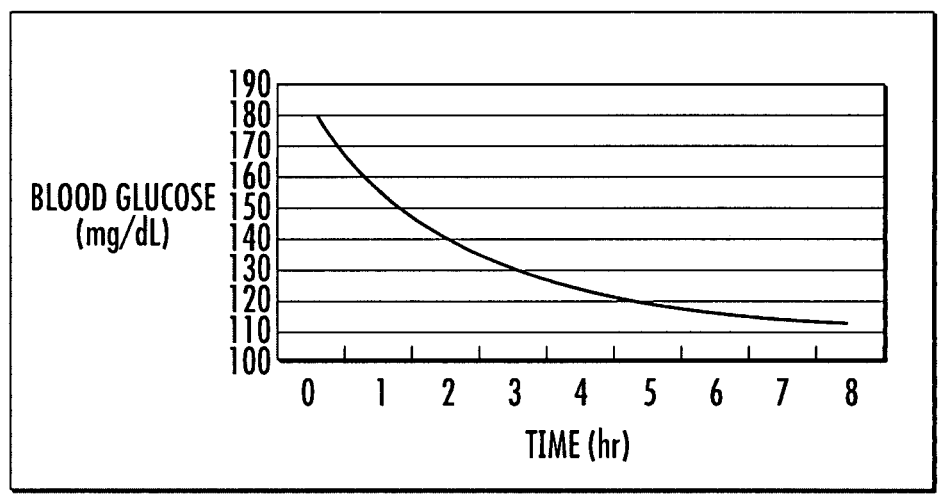
FIG. 21 is a graph of blood glucose concentration versus time with continuous monitoring and real-time insulin infusion rate reassignment according to an embodiment of the subject matter disclosed herein.

Substituting the value of C into the equation, the resulting specific solution giving future BG as function of time is graphed in FIG. 21. FIG. 21 is a BG versus time graph of idealized prediction with continuous monitoring and real-time insulin infusion rate reassignment. The data shown in the graph is derived from the following equation:

$$\ln(BG-BG_{upper\ target}) = -(ROD_{@BGcritical\ high})*(t)/(BG_{critical\ high}-BG_{upper\ target})+\ln(BG_{starting}-BG_{upper\ target})$$

In FIG. 21, the idealized prediction of BG as a function of time is shown for the default adult values $BG_{critical\ high}=180$ mg/dL, $ROD_{@BGcritical\ high}=30$ mg/dL per hour, and $BG_{upper\ target}=110$ mg/dL, with a starting BG of 180 mg/dL at time zero.

Future BG as a function of time during descent of BG, with real-time insulin infusion rate assignment may be defined by the following equation:

$$BG = BG_{upper\ target} + (BG_{starting} - BG_{upper\ target}) * e^{[-(ROD@BGcritical\ high)*(t)/(BGcritical\ high-BGupper\ target)]}$$

Suppose $BG_{starting} > BG_{upper\ target}$, if $BG_{starting}$ is the starting BG, then the time to half-correction of BG ($time_{half\ correction}$) is defined as the time when:

$$(\tfrac{1}{2})*(BG_{starting}-BG_{upper\ target}) = BG-BG_{upper\ target}$$

The BG as a variable and the value of $BG_{starting}$ both drop out of the expression for time to half-correction of $BG_{starting}$ to result in the following equation:

$$\text{timehalf correction} = (\ln 2)*(BG_{critical\ high}-BG_{upper\ target})/(ROD_{@BG\ critical\ high})$$

Suppose that continuous revision of ROD occurs (driven by a fictitious BG sensing and insulin delivery system that achieves $ROD_{ideal,next}$ at every time point), then counting from time zero, as the future BG approaches target, the time for future half-correction of $BG_{starting}$ is provided by, for the defaults $BG_{critical\ high}$=180 mg/dL, $ROD_{@BGcritical\ high}$=30 mg/dL-hr, and $BG_{upper\ target}$=110 mg/dL, $time_{half\ correction}$=1.617 hr.

Future BG Prediction and Time-to-Half Correction During Euglycemia with Continuous BG Monitoring and Continuous Revision of $ROA_{ideal,next}$ Under the assumption of a perfect closed loop system, a similar equation for future BG as a function of time, and a similar calculation for $time_{half\ correction}$, may be made during ascent of BG toward $BG_{true\ target}$, from a euglycemic starting value for $BG_{starting}$. Assuming $70 \leq BG < BG_{true\ target}$ during ascent the following equations apply:

$$d(BG)/(dt)=ROA=(ROA_{max})*(BG_{true\ target}-BG)/(BG_{true\ target}-70)$$

$$d(BG)/(BG_{true\ target}-BG)=[(ROA_{max})/(BG_{true\ target}-70)]*(dt)$$

$$-\ln(BG_{true\ target}-BG)=[(ROA_{max})/(BG_{true\ target}-70)]*(t)+C$$

$$BG_{true\ target}-BG=e^{-[(ROAmax)/(BGtrue\ target-70)]*(t)-C}$$

To define the constant C by looking at one point having given conditions, the time may be said to be zero when the value of BG as a variable equals $BG_{starting}$ (i.e. $BG=BG_{starting}$), where boundary conditions→[($BG_{starting}$)ln mg/dL,(zero)in hr]

Figure 22:
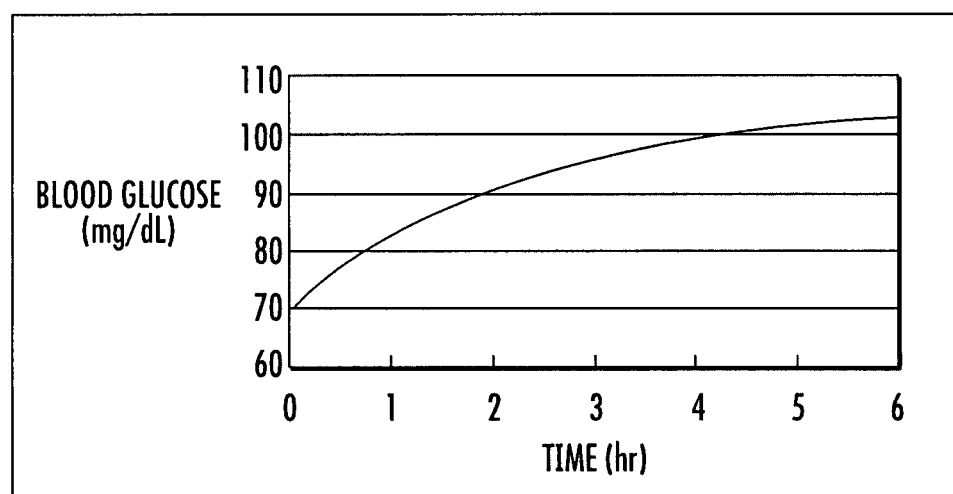
FIG. 22 is a graph of blood glucose versus time according to an embodiment of the subject matter disclosed herein.

$BG_{true\ target}-BG_{starting}=e$ raised to the power$^{(-C)}$ $C=-\ln(BG_{true\ target}-BG_{starting})$ Substituting the value of C into the equation, the resulting specific solution giving future BG as a function of time is graphed in FIG. 22 and is derived from the following equations:

$$BG_{true\ target} - BG = e^{-[(ROAmax)/(BGtrue\ target)-70)]*(t)+\ln(BGtrue\ target-BGstarting)]}$$

$$BG_{true\ target} - BG = e^{\ln(BGtrue\ target-BGstarting)} / e^{[(ROAmax)/(BGtrue\ target-70)]*(t)}$$

In FIG. 22, an idealized prediction of BG as a function of time is shown for the default adult values $BG_{true\ target}$=105 mg/dL and $ROA_{max}$=17.5 mg/dL per hour, with a starting $BG_{starting}$ of 70 mg/dL at time zero.

Future BG as a function of time during ascent of BG with real-time insulin infusion rate reassignment may be defined by the following equation:

$$BG=BG_{true\ target}-(BG_{true\ target}-BG_{starting})/e^{(ROAmax)*(t)/(BGtrue\ target-70)}$$

Suppose $70 \leq BG_{starting} < BG_{true\ target}$, if $BG_{starting}$ is the starting BG, then the time to half-correction of BG ($time_{half\ correction}$) is defined as the time when:

$$(½)*(BG_{true\ target}-BG_{starting})=(BG_{true\ target}-BG)$$

The BG as a variable and the value of $BG_{starting}$ both drop out of the expression for time to half-correction of $BG_{starting}$ such that:

$$Time_{half\ correction}=\ln 2*(BG_{true\ target}-70)/(ROA_{max})$$

For the defaults $ROA_{max}$=17.5 mg/dL per hour and for $BG_{true\ target}$=105 mg/dL, $time_{half\ correction}$=1.386294 hr.

Definitions and Default Values

Blood glucose related definitions and default values follow:
$BG_{true\ target}$, calculated, mg/dL 70+(105−70)*(alternative given $_{BGupper\ target}$−70)/(110−70)
$BG_{upper\ target}$, calculated, mg/dL 70+(105−70)*(alternative given $BG_{true\ target}$−70)/(110−70)
$BG_{critical\ high}$, calculated, mg/dL 70+(180−70)*(alternative $_{BGtrue\ target}$−70)/(105−70)
$BG_{lower\ target}$, calculated, mg/dL 70+(80−70)*(alternative $BG_{true\ target}$−70)/(105−70)
$BG_{true\ target}$ 105 mg/dL, given, default for adults;
  120 mg/dL, given, default for children, GFR <30 cc/min, or BG<50 within 24 hr prior to algorithm initiation or during the treatment course (user-defined higher default values may be entered by caregiver);
  value calculated as defaults alternative $BG_{upper\ target}$:
  183.75 mg/dL for adults with diabetic ketoacidosis (calculated),
  227.5 for pediatric patients with diabetic ketoacidosis (calculated),
  271.25 for adults with HHS (calculated)
$BG_{upper\ target}$ 110 mg/dL, given, default for adults
  200 mg/dL for adults with diabetic ketoacidosis (given);
  250 mg/dL for pediatric patients with diabetic ketoacidosis (given);
  300 mg/dL for adults with HHS (given);
  values calculated as defaults for alternative $BG_{true\ target}$:
  127 mg/dL, calculated, for children, GFR<30 cc/min, or BG<50 within 24 hr prior to algorithm initiation or during the treatment course
$BG_{critical\ high}$ >180 mg/dL, given, default for adults values calculated as defaults for alternative $BG_{true\ target}$:
  >227 mg/dL for children (calculated);
  427.5 mg/dL for adults with diabetic ketoacidosis (calculated);
  565.00 for pediatric patients with diabetic ketoacidosis (calculated);
  702.50 for adults with HHS (calculated)
$BG_{lower\ target}$ 80 mg/dL, given, default for adults;
  150 mg/dL for adults with diabetic ketoacidosis (given);
  150 mg/dL for pediatric patients with diabetic ketoacidosis (given);
  250 mg/dL for adults with HHS (given);
  values calculated as defaults for alternative $BG_{true\ target}$:
  84 mg/dL, calculated, for children, GFR<30 cc/min, or BG<50 within 24 hr prior to algorithm initiation or during the treatment course
Acceptable target range BG 80-110 mg/dL for adults
  84-127 mg/dL for children, GFR<30 cc/min, or BG<50 within 24 hr
  prior to algorithm initiation or during the treatment course:
  150-200 for DKA for adults;
  150-250 for DKA for children;
  250-300 for adults with HHS
Hypoglycemia BG<70 mg/dL
$ROD_{ideal,next,max}$ maximum rate of descent of BG that can be assigned as $ROD_{ideal,next}$;
  default rate assigned as 70 mg/dL per hr;
  alternative default=150 mg/dL per hr for adults with diabetic ketoacidosis and HHS;
  this value is used even if the linear equation for $ROD_{ideal,next}$ gives a higher value;

this value used as the asymptote for the negative exponential equation $ROD_{@BG\ critical\ high}$ ideal rate of descent of BG at critical high BG;
   default=30 mg/dL per hr;
   alternative default=75 mg/dL per hr for diabetic ketoacidosis and HHS G-per-Diem glucose flux per daily dose of insulin, exogenously mediated;
   Default value=1800 mg/dL $ROA_{max}$ population average maximum rate of ascent of BG, Observable at BG=70 mg/dL, after correction of any hypoglycemia;
   assumed rate of ascent 17.5 mg/dL per hr for trauma service patients;
   assumed rate of ascent 35 mg/dL per hr for DKA and HHS during recovery;

MR related definitions and default values follow:
$MR_{initial}$ initial estimated MR
   (among adults, normally 2 units/hr for trauma service, burn unit, corticosteroid-treated patients, or severely stressed patients; default normally 1 unit/hr for all others; for children 0.015 units/kg-hr)

Infusion rate of insulin at BG 70 mg/dL definitions and default values follow:
$IR_{@BG70}$ 0.1 units/hr for adults;
   0.002 units/kg per hr for children (or off until $testtime_{next}$, if the calculated rate is below the minimum delivery capability of the syringe pump)

Maximum rate of insulin infusion definitions and default values follow:
$IR_{max}$ 36 units per hr for adults and 0.54 units/kg per hr for children

Other Definitions

Treatment course a treatment course is a sequence of consecutive days on which input to the systems and methods (or algorithm) described herein was provided for at least part of every calendar date under a single original or renewed intravenous insulin infusion order;
   Input may be defined by discovery of a web-based nursing entry, made at some time subsequent to the first algorithm output that initiated the treatment course, and documenting a previous insulin infusion rate by statement of the start time for that rate and units/hr Iteration segment of a treatment course of use of insulin algorithm between the times of $BG_{previous}$ and $BG_{current}$ It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A system for determining an intravenous insulin infusion rate to correct hyperglycemia of a patient, the system comprising:
   (a) a measurement receiver configured to receive a glycemic measurement of a patient; and
   (b) an insulin infusion rate calculator configured to:
      (i) estimate a maintenance rate (MR) of insulin infusion to maintain euglycemia in the patient;
      (ii) determine a relationship between a current blood glucose concentration of the patient and a target blood glucose concentration;
      (iii) determine an MR-dependent insulin infusion rate (IR) based on the estimated MR and based on the relationship between the current blood glucose concentration and the target blood glucose concentration, wherein determining the MR-dependent IR includes assigning the patient to an iso-MR function that defines a relationship between IR values and blood glucose concentrations based on distance from target, and which during hyperglycemia is based on an ideal rate of descent of blood glucose concentration;
      (iv) measure a glycemic response of the patient while using the determined IR;
      (v) re-estimate the MR based on the glycemic response of the patient at a previous IR; and
      (vi) repeatedly perform steps (ii)-(v), wherein the estimated MR in step (v) during each $n^{th}$ iteration is utilized to determine the IR in step (iii) of each $(n+1)^{th}$ iteration, n being an integer.

2. The system of claim 1 wherein the insulin infusion rate calculator is configured to identify the iso-MR function from a plurality of iso-MR functions that provides the IR as a function of blood glucose concentration, wherein the functions are each associated with different MR values.

3. The system of claim 2 wherein the insulin infusion rate calculator is configured to receive input regarding the patient condition of the patient, and configured to enter predetermined parameter values, based on a condition of the patient, that will identify a family of functions for a next IR for the patient such that the functions differ within the family according to the MR, wherein the members of a family of functions are the same with respect to target blood glucose concentrations ($BG_{upper\ target}$, $BG_{true\ target}$, and $BG_{lower\ target}$), $BG_{critical\ high}$, $IR_{@BG70}$, $ROD_{@BGcritical\ high}$, and $ROD_{ideal,next,max}$.

4. The system of claim 3 wherein one of the families is associated with general hospital care; one of the families diabetic ketoacidosis, and wherein one of the families is associated with hyperglycemic hyperosmolar state.

5. The system of claim 1 wherein the insulin infusion rate calculator is configured to estimate the MR using the following equation during hyperglycemia:

$$MR_{case} = IR_{previous} / [1 + 24 * ([ROD_{previous,revised}]/[G\text{-}per\text{-}\text{Diem}])$$

wherein $MR_{csne}$ is the maintenance rate, $IR_{previous}$ is an insulin infusion rate at a previous iteration of steps (b)-(e), $ROD_{previous}$ is a rate of descent of the blood glucose concentration of the patient at the previous iteration including one of positive and negative values and defined as having non-zero value for BG above a target value, and G-per-DIEM is a glucose flux per daily dose of insulin.

6. The system of claim 1 wherein at least functions (i), (ii), (iv), (v), and (vi) are automated.

7. A system for determining an intravenous insulin infusion rate to maintain euglycemia of a patient, the system comprising:
   (a) a measurement receiver configured to receive a glycemic measurement of a patient; and
   (b) an insulin infusion rate calculator configured to:
      (i) estimate a maintenance rate (MR) of insulin infusion to maintain euglycemia in the patient;
      (ii) determine a relationship between a current blood glucose concentration of the patient and a target blood glucose concentration;
      (iii) determine an MR-dependent insulin infusion rate (IR) based on the estimated maintenance rate, wherein determining the MR-dependent IR includes assigning the patient to an iso-MR function that defines a relationship between IR values and blood glucose concentrations based on distance of blood glucose from target and, in case of hyperglycemia, based on an ideal rate of descent of blood glucose concentration;

(iii) measure a glycemic response of the patient to an insulin infusion given to the patient using the determined IR;

(iv) re-estimate the MR based on the glycemic response of the patient; and (v) repeatedly perform functions (ii)-(iv), wherein the estimated MR in function (iv) during each $n^{th}$ iteration is utilized to calculate the IR in function (ii) of each $(n+1)^{th}$ iteration, n being an integer.

* * * * *